(12) United States Patent
Pollock et al.

(10) Patent No.: US 6,319,495 B1
(45) Date of Patent: Nov. 20, 2001

(54) METHOD FOR RESTORING GLUCOSE RESPONSIVENESS TO INSULIN SECRETION

(75) Inventors: Allan S. Pollock, San Francisco, CA (US); Sylvia Christakos, Mendham, NJ (US); Daphne Reddy, Redwood City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/051,696

(22) PCT Filed: Oct. 17, 1996

(86) PCT No.: PCT/US96/16736

§ 371 Date: Nov. 30, 1998

§ 102(e) Date: Nov. 30, 1998

(87) PCT Pub. No.: WO97/14441

PCT Pub. Date: Apr. 24, 1997

Related U.S. Application Data

(60) Provisional application No. 60/005,386, filed on Oct. 18, 1995.

(51) Int. Cl.[7] ............... A01N 63/00; C12P 21/06; C12N 5/00; C12N 15/63; C07H 21/04
(52) U.S. Cl. ............... 424/93.21; 424/93.2; 435/69.1; 435/320.1; 435/325; 435/455; 536/23.5
(58) Field of Search ............... 424/93.1, 425, 424/93.21, 93.2; 435/325, 69.1, 455; 536/23.1

(56) References Cited

U.S. PATENT DOCUMENTS 5,811,266 * 9/1998 Newgard ............... 435/69.4

OTHER PUBLICATIONS

Mcdonald et al, Mol. Cell. Endocrin. 123(2):199–204, 1996.*
Efrat. Diabetologia. 41:1401–1409, 1998.*

* cited by examiner

*Primary Examiner*—Deborah J. R. Clark
*Assistant Examiner*—Sumesh Kaushal
(74) *Attorney, Agent, or Firm*—Townsend and Townsend and Crew LLP

(57) ABSTRACT

This invention comprises engineered cells that express a nucleic acid that encodes a calbindin molecule, and exhibit the ability to secrete insulin in a glucose-sensitive fashion. This invention also comprises an artificial tissue that, when implanted into recipients that do not secrete insulin in a glucose-sensitive fashion, imparts to the recipients the ability to secrete insulin in a glucose-sensitive fashion. The artificial tissue comprises engineered cells that express a nucleic acid that encodes a calbindin molecule and secrete insulin in a glucose-sensitive fashion, enclosed by a semi-permeable porous matrix.

19 Claims, 3 Drawing Sheets

METHOD FOR RESTORING GLUCOSE RESPONSIVENESS TO INSULIN SECRETION

This Application claims priority from Provisional Application Ser. No. 60/005,386, filed Oct. 18, 1995.

The government may have certain rights in the present invention pursuant to NIH grants DK38961 and DK31398.

BACKGROUND OF THE INVENTION

A. Field of the Invention

The present invention relates generally to the field of genetic engineering and gene expression. More specifically, it relates to artificial tissues, particularly to artificial tissues comprising engineered cells having the ability to secrete insulin in a glucose-sensitive fashion. It also relates to the use of engineered cells in the production of human insulin for use in, for example, the treatment of insulin deficient conditions such as type I diabetes mellitus.

B. Description of the Related Art

The β cells of the pancreatic islets of Langerhans synthesize insulin. A portion of this insulin is slowly and continually released into the bloodstream (basal secretion). However, the bulk of the insulin is stored in secretory vesicles and released only in response to certain physiological stimuli (stimulated secretion).

In humans and other mammals, the principal physiological stimulus for the secretion of insulin is increased blood levels of glucose (e.g., following ingestion of a carbohydrate meal). The capacity of normal islet β cells to sense a rise in blood glucose concentration and to respond by secreting insulin is critical to control of blood glucose levels.

In certain insulin-deficient conditions such as diabetes mellitus, the pancreas loses its ability to manufacture and secrete insulin in response to rising blood glucose concentrations. The result is a metabolic imbalance, which causes blindness, kidney-related diseases, neurological disorders, cardiovascular diseases, non-accidental amputation of limbs, and death.

The current preferred treatment for insulin deficiency is injection of insulin once or twice daily. The objective of this regimen is to maintain glucose levels close to normal. However, daily insulin injections can not reproduce the rapid insulin secretory responses of normal islets to physiological demand. Most insulin deficient patients never achieve the finely-tuned glucose homeostasis needed to avoid long-term complications.

Consequently, a major goal of research into insulin deficiencies is to develop a system for sensing changes in blood glucose and quickly adjusting insulin output to maintain normal blood glucose levels at all times. One approach has been replacement of the malfunctioning organ by transplantation of normal pancreatic tissue. Lacy et al. (1986), *Ann. Rev. Med.*, 37: 33–40; Lacey (July, 1995), *Scientif. Amer.* 273: 50–55. However, transplanted islets are recognized and destroyed by the same autoimmune mechanism responsible for destruction of the patient's original β cells. For this reason artificial pancreatic devices containing live islets have often been designed to avoid immune rejection, often by enclosing islets in a semipermeable pouch or matrix which separates the transplanted islets from immunoreactive cells and molecules.

The treatment of diabetes with peritoneal implants of encapsulated islets in vivo diabetic models has been reported by several research groups. Lum et al. (1991), "Prolonged reversal of diabetic state in NOD Mice by xenografts of microencapsulated rat islets," *Diabetes*, 40: 1511; and Maki et al. (1991), "Successful treatment of diabetes with the biohybrid artificial pancreas in dogs," *Transplantation*, 51: 43; Scharp etal. (1990), "Insulin independence after islet transplantation into type I diabetic patient," *Diabetes*, 39: 515; Robertson (1991), "Pancreas Transplantation in humans with diabetes mellitus," Diabetes, 40: 1085; Colton et al. (1991), "Bioengineering in development of the hybrid artificial pancreas," *J. Biomech. Eng.*, 113: 152; Reach (1990), "Bioartificial pancreas: Status and bottlenecks," *Intern. J. Art. Organs*, 13: 329; and Warnock et al. (1988), "Critical mass of purified islets that induce normoglycemia after implantation into dogs," *Diabetes*, 37: 467. See also, T. Matsumura (U.S. Pat. No. 3,827,565); Sun et al. (U.S. Pat. No. 4,323,457 (1982)); Chick etal. (U.S. Pat. Nos. 4,242,459 and 4,242,460 (1980)); Lim, U.S. Pat. No. 4,391,909; Loeb, U.S. Pat. No. 4,378,016; Newgard, U.S. Pat. No. 5,427,940 (1992); Bae, et. al., U.S. Pat. No. 5,262,055 (1993).

SUMMARY OF THE INVENTION

The present invention comprises an engineered cell that secretes insulin in a glucose-sensitive fashion and that further expresses a drug sensitivity. This engineered cell expresses a first exogenous nucleic acid that encodes a calbindin molecule and a second exogenous nucleic acid that encodes a drug sensitivity, with the proviso that in the absence of said first exogenous nucleic acid that encodes a calbindin molecule, the host cell does not secrete insulin in glucose-sensitive fashion. The engineered cell may be a primary isolate, a continuous non-transformed cell line, or an insulinoma, preferably of human origin. The engineered cell may optionally be negatively selected by exposure to metabolites or drugs that are lethal to cells that express the drug sensitivity gene.

The invention further encompasses a method for imparting glucose-sensitive insulin secretion to a host cell that does not exhibit glucose-sensitive insulin secretion, comprising the steps of a) providing a cell that is capable of producing and secreting insulin, but has an impaired ability to secrete insulin in a glucose sensitive fashion; and b) stably introducing into said cell a nucleic acid that encodes a calbindin molecule, wherein the expression of said nucleic acid that encodes a calbindin molecule imparts to the engineered host cell the ability to secrete insulin in a glucose-sensitive fashion. In different embodiments of this method, the mammal is a human patient, the engineered cell is either conspecific or syngeneic with the mammal into which it is stably introduced, and the cell is selected from the group consisting of a primary isolate, a continuous non-transformed cell line or an insulinoma.

Other embodiments of this invention are artificial implantable tissues that secrete insulin in response to humoral signals, in particular glucose. One such embodiment is an engineered cell that expresses calbindin and secretes insulin in a glucose-sensitive fashion, wherein the cell is enclosed in a semipermeable matrix or membrane that permits the diffusion of glucose and nutrients into the matrix, and the diffusion of insulin and waste products out of the matrix. The matrix may be formed from plasma, fibrinogen, casein, fibrin, limulus lysate, milk protein, collagen, agarose, carrageenan, agar, alginate, guar gum, gum arabic, pectin, tragacanth gum, xanthan gum, and mixtures thereof. These matrix-enclosed engineered glucose-sensitive insulin-secreting calbindin-expressing cells are implanted or injected into an animal that is unable to secrete insulin in a glucose-sensitive fashion.

In one embodiment, a cell-containing matrix of this invention is prepared by: (1) polymerizing matrix components or precursors in the presence of viable engineered cells that express an exogenous calbindin and secrete insulin in a glucose-sensitive fashion, and (2) recovering a porous matrix containing viable cells. Depending upon which components are used to make the matrix, the polymerization can be achieved by exposing the respective precursor to a polymerization promoting reagent and/or a polymerization promoting condition.

In another embodiment, the current invention provides methods for growing artificial β cells in liquid culture and for the increased production of human insulin by perfusion of such recombinant cells with glucose-containing buffers.

DETAILED DESCRIPTION OF THE INVENTION

Figure 1:
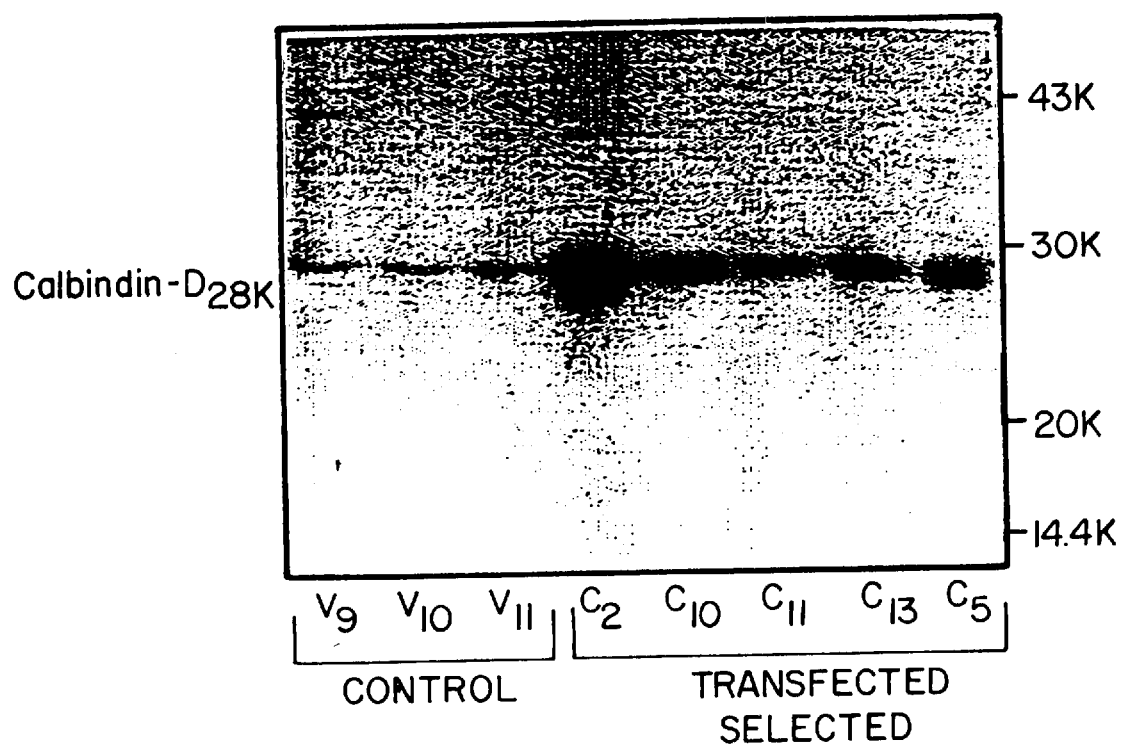
FIG. 1. Western blot analysis of cells that express calbindin

The presently-available implantable artificial pancreatic devices suffer from problems of donor availability, tissue typing, and recovery and replacement of cells. These problems are addressed herein by the provision of renewable stocks of tissue culture cells that secrete insulin in a glucose-sensitive fashion.

The patents and publications cited in this disclosure reflect the level of skill the art to which this invention pertains, and are herein individually incorporated by reference to the extent that they supplement, explain, provide a background for or teach methodology, techniques and/or compositions employed herein.

Unless defined otherwise, all technical and scientific terms used herein have the same meaning as commonly understood by one of ordinary skill in the art to which this invention belongs. Singleton et al. (1994), DICTIONARY OF MICROBIOLOGY AND MOLECULAR BIOLOGY, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A. Definitions

The phrase "secretes insulin in a glucose-sensitive fashion" denotes that, in response to concentrations of glucose that range from about 5 mM to about 20 mM or above, a cell secretes insulin at a rate and to an extent that exceeds basal secretion. When the glucose concentration is below this range, essentially the only insulin secreted is basal secretion. Glucose-sensitive stimulated secretion is triggered by glucose concentrations in the above mentioned range, and ceases when the glucose concentrations fall below this range.

The phrase "impaired ability to secrete insulin in a glucose-sensitive fashion" refers to a cell or organism that cannot secrete insulin (i.e., because the β cells are absent or dysfunctional), or that cannot secrete insulin in a glucose-sensitive fashion.

The term "nucleic acid" refers to a deoxyribonucleotide or ribonucleotide polymer in either single- or double-stranded form, and unless specifically limited, encompasses known analogues of natural nucleotides that hybridize to nucleic acids in manner similar to naturally occurring nucleotides. Unless otherwise indicated, a particular nucleic acid sequence implicitly provides the complementary sequence thereof, as well as the sequence explicitly indicated. The terms "nucleic acid" and "gene" are used interchangeably and they encompass "cDNA."

The phrase "exogenous nucleic acid" generally denotes a nucleic acid that has been isolated, cloned and introduced into or expressed in a cell or cellular environment other than the cell or cellular environment in which said nucleic acid or protein may be found in nature. The term encompasses both nucleic acids originally obtained from a different organism or cell type than the cell type in which it is expressed, and also nucleic acids that are obtained from the same cell line as the cell line in which it is expressed. As used herein, "expression" or "expressed" refers to transcription of nucleic acids, either without or with subsequent translation.

The phrase "a nucleic acid sequence encoding" refers to a nucleic acid which contains sequence information that, if translated, yields the primary amino acid sequence of a specific protein or peptide. This phrase specifically encompasses degenerate codons (i.e., different codons which encode a single amino acid) of the native sequence or sequences which may be introduced to conform with codon preference in a specific host cell.

The term "calbindin" denotes a family of genes and gene products which specifically encompasses the gene and gene product of the calbindin-$D_{28k}$ ($CaBP_{28k}$) or calbindin-D9K cDNA and conservatively modified variants thereof. Calbindin further denotes nucleic acid sequences and their gene products wherein the gene products bind calcium and are recognized by antibodies that specifically bind to the gene product of $CaBP_{28k}$ cDNA. For a discussion of the calbindin family of proteins, see e.g., Christakos et al. (1989), Vitamin D-dependent calcium binding proteins: chemistry, distribution, functional considerations, and molecular biology. Endocrine Reviews 10(1): 3–26; Christakos, S. Vitamin D-dependent calcium binding proteins: chemistry, distribution, functional considerations, and molecular biology: update 1995. in D. D. Bikle, ed. HORMONAL REGULATION OF BONE AND MINERAL METABOLISM. V4, p84–107 (1995). The sequences for the various calbindins have been reported in the literature, and are hereby incorporated by reference. The sequences of two calbindins, rat D28 and human D27, are included as sequence ID No 1 and No 2, for exemplary purposes.

The phrase "expresses a drug sensitivity" signifies 1) that a cell is rendered susceptible to one or more specific chemical substances by virtue of expressing a gene product that is capable of producing a cytotoxic chemical substance, or 2) that a cell that contains an inducible gene (i.e., placed under the control of an inducible promoter) whose gene product is itself cytotoxic. For example, the enzyme cytosine deaminase converts 5-fluorocytosine ("5FC") into the lethal metabolite 5-fluorouracil ("5FU"). Host cells that are induced to produce cytosine deaminase by virtue of having the cytosine deaminase gene introduced into and expressed in the host cell, when exposed to 5FC, will die as a result of the formation of 5FU. Another gene that confers drug sensitivity upon a host cell is the thymidine kinase gene, which confers sensitivity to gancyclovir. See: Ido et al. (1995), *Cancer Research*, 55: 3105; lzquierdo et al. (1995), *Gene Therapy*, 2: 66. Other such "drug sensitivity" or "suicide" genes are known in the art, and are expressly encompassed by the present invention. "Negative selection" signifies that the cells that contain and express the drug sensitivity gene and are exposed to substances to which the gene confers sensitivity are consequently selectively destroyed or their growth or development is significantly impaired relative to that of cells which do not express the gene.

The term "con-specific" indicates that two cells or cell lines or a cell line and an organism are from the same animal species. The term "syngeneic" means that two cells or a cell and an organism are from the same individual.

The term "recombinant" or "engineered" when used with reference to a nucleic acid or a protein generally denotes that the composition or primary sequence of said nucleic acid or protein has been altered from the naturally occurring sequence using experimental manipulations well known to those skilled in the art. It may also denote that a nucleic acid or protein has been isolated and cloned into a vector, or a nucleic acid that has been introduced into or expressed in a cell or cellular environment other than the cell or cellular environment in which said nucleic acid or protein may be found in nature.

The term "recombinant" or "engineered" when used with reference to a cell indicates that the cell replicates or expresses a nucleic acid or expresses a peptide or protein encoded by a nucleic acid, whose origin is exogenous to the cell. Recombinant cells can express nucleic acids that are not found within the native (non-recombinant) form of the cell. Recombinant cells can also express nucleic acids found in the native form of the cell wherein the nucleic acids are re-introduced into the cell by artificial means.

The term "vector" denotes an engineered nucleic acid construct that contains sequence elements that mediate the replication of the vector sequence and/or the expression of coding sequences present on the vector. Examples of vectors include eukaryotic and prokaryotic plasmids, viruses, cosmids, phagemids, and the like. The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence. One or more selected isolated nucleic acids may be operably linked to a vector by methods known in the art.

"Engineered" or "transduction" or "transfection" denotes a group of processes whereby an exogenous nucleic acid is introduced into a cell, such that the cell is capable of replicating and/or expressing the exogenous nucleic acid. Generally, a selected nucleic acid is first inserted into a vector and the vector is then introduced into the cell. For example, plasmid DNA that is introduced under appropriate environmental conditions may undergo replication in the engineered cell, and the replicated copies are distributed to progeny cells when cell division occurs. As a result, a new cell line is established, containing the plasmid and carrying the genetic determinants thereof. Transduction by a plasmid in this manner, where the plasmid genes are maintained in the cell line by plasmid replication, occurs at high frequency when the transducting plasmid DNA is in closed loop form, and does not or rarely occurs if linear plasmid DNA is used.

"Stably expressed" indicates that the exogenous nucleic acid is expressed in a host cell essentially for the life of the cell, and that the progeny of the engineered cell, if any, also express the exogenous nucleic. Stable expression may be the consequence of integration of the nucleic acid into the host cell genome. Alternatively, the vector that comprises the nucleic acid may be replicated and transmitted episomally.

"Stably introducing" a cell or cell line into an organism means that the cell or cell line is injected or implanted into the organism, for example intraperitoneally, into the blood, or into vascularized tissue, and that the cell or cell line is able to survive and perform for extended periods of time, measured in weeks, preferably months, and most preferably years.

B. General Methods for Introduction of Calbindin in Cells

An important aspect of this invention are methods for introducing calbindin into insulin-producing cells. Standard eukaryotic transduction methods are used to produce cell lines which express calbindin and, optionally, a drug resistance gene. It is expected that those of skill in the art are knowledgeable in the numerous systems available for cloning and expressing nucleic acids.

In brief summary, the expression of natural or synthetic nucleic acids is typically achieved by operably linking a nucleic acid of interest (e.g., one encoding calbindin) to a promoter (which is either constitutive or inducible) and incorporating the construct into an expression vector. The vectors are suitable for replication and integration in prokaryotes, eukaryotes, or preferably both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, Giliman and Smith (1979), *Gene*, 8: 81–97; Roberts et al. (1987), *Nature*, 328: 731–734; Berger and Kimmel, *Guide to Molecular Cloning Techniques, Methods in Enzymology*, volume 152, Academic Press, Inc., San Diego, Calif. (Berger); Sambrook et al. (1989), MOLECULAR CLONING—A LABORATORY MANUAL (2nd ed.) Vol. 1–3, Cold Spring Harbor Laboratory, Cold Spring Harbor Press, N.Y., (Sambrook); and Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The expression vector typically comprises a eukaryotic transcription unit or expression cassette that contains all the elements required for the expression of exogenous calbindin in eukaryotic cells. A typical expression cassette contains a promoter operably linked to the DNA sequence encoding a calbindin protein and signals required for efficient polyadenylation of the transcript.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Press, Cold Spring Harbor, N.Y. 1983, which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the calbindin structural gene to provide for efficient termination. The termination region may be obtained from the same source as the promoter sequence or may be obtained from a different source.

If the mRNA encoded by the calbindin structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned nucleic acids or to facilitate the identification of cells that carry the transduced DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transduced DNA integrates into the genome of the engineered cell, where the promoter directs expression of the desired nucleic acid.

The vectors usually comprise selectable markers which result in nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a bacculovirus vector in insect cells, with calbindin encoding sequence under the direction of the polyhedrin promoter or other strong baculovirus promoters.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Once a nucleic acid is synthesized or isolated and inserted into a vector and cloned, one may express the nucleic acid in a variety of recombinantly engineered cells known to those of skill in the art. Expression of a an exogenous nucleic acid can be enhanced by including multiple copies of, for example, a calbindin-encoding nucleic acid in an engineered cell, by selecting a vector known to reproduce in the host, thereby producing large quantities of protein from exogenous inserted DNA (such as pUC8, ptac12, or pIN-III-ompA1, 2, or 3), or by any other known means of enhancing peptide expression. Calbindin molecules will be expressed when the DNA sequence is functionally inserted into a vector. "Functionally inserted" means that it is inserted in proper reading frame and orientation and operably linked to proper regulatory elements. Typically, a calbindin gene will be inserted downstream from a promoter and will be followed by a stop codon, although production as a hybrid protein followed by cleavage may be used, if desired.

C. Useful Vectors for Introduction and Expression of Calbindin in Cells

Vectors to which calbindin-encoding nucleic acids are operably linked may be used to introduce these nucleic acids into host cells and mediate their replication and/or expression. "Cloning vectors" are useful for replicating and amplifying the foreign nucleic acids and obtaining clones of specific foreign nucleic acid-containing vectors. "Expression vectors" mediate the expression of the foreign nucleic acid. Some vectors are both cloning and expression vectors.

In general, the particular eukaryotic expression vector used to transport calbindin or any other gene into the cell is not particularly critical. Any of the conventional vectors used for expression in eukaryotic cells may be used. Expression vectors containing regulatory elements from eukaryotic viruses such as retroviruses are typically used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

While a variety of vectors may be used, it should also be noted that viral vectors such as retroviral vectors are useful for modifying eukaryotic cells because of the high efficiency with which the retroviral vectors transfect target cells and integrate into the target cell genome. Additionally, the retroviruses harboring the retroviral vector are capable of infecting cells from a wide variety of tissues.

Retroviral vectors are produced by genetically manipulating retroviruses. Retroviruses are RNA viruses because the viral genome is RNA. Upon infection, this genomic RNA is reverse transcribed into a DNA copy which is integrated into the chromosomal DNA of transfected cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C. (1983), In: *Experimental Manipulation of Gene Expression*, M. Inouye (ed), 155–173; Mann et al. (1983), *Cell*, 33: 153–159; Cone, R. D. and R. C. Mulligan (1984), *Proceedings of the National Academy of Sciences, U.S.A.*, 81: 6349–6353.

The design of retroviral vectors is well known to one of skill in the art. See Singer, M. and Berg, P., supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa (1986), *Biotechniques*, 4: 504–512, Mann et al. (1983), *Cell*, 33: 153–159, Cone and Mulligan (1984), *Proc. Natl. Acad. Sci. USA*, 81: 6349–6353, Eglitis et al. (1988), *Biotechniques*, 6: 608–614, Miller et al. (1989), *Biotechniques*, 7: 981–990, Miller, A. D. (1992), *Nature*, supra, Mulligan, R. C. (1993), supra, and Gould et al., and International Patent Application No. WO 92/07943 entitled "Retroviral Vectors Useful in Gene Therapy." The teachings of these patents and publications are incorporated herein by reference.

The retroviral vector particles are prepared by recombinantly inserting a nucleic acid encoding a calbindin molecule and optionally a drug sensitivity gene into a retrovirus vector and packaging the vector with retroviral capsid proteins by use of a packaging cell line. The resultant retroviral vector particle is generally incapable of replication in the host cell and is capable of integrating into the host cell genome as a proviral sequence containing the calbindin nucleic acid. As a result, the patient is capable of producing calbindin and optionally the gene product of the drug sensitivity gene.

Packaging cell lines are generally used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transducing a cell line with one or more expression plasmids encoding the appropriate core and envelope proteins. In these cells, the gag, pol, and env genes can be derived from the same or different retroviruses.

A number of packaging cell lines suitable for the present invention are available in the prior art. Examples of these cell lines include Crip, GPE86, PA317 and PG13. See Miller etal. (1991), *J. Virol.*, 65: 2220–2224, which is incorporated herein by reference. Examples of other packaging cell lines are described in Cone, R. and Mulligan, R. C. (1984), *Proceedings of the National Academy of Sciences, U.S.A.*, 81: 6349–6353 and in Danos, O. and R. C. Mulligan (1988), *Proceedings of the National Academy of Sciences, U.S.A.*, 85: 6460–6464, Eglitis et al. (1988), *Biotechniques*, 6: 608–614, Miller, A. D. et al. (1989), *Biotechniques*, 7: 981–990, also all incorporated herein by reference. Amphotropic or xenotropic envelope proteins, such as those produced by PA317 and GPX packaging cell lines may also be used to package the retroviral vectors.

In addition to the retroviral vectors mentioned above, cells may be transfected with adeno-associated viral vectors. See, e.g., *Methods in Enzymology*, Vol. 185, Academic Press, Inc., San Diego, Calif. (D. V. Goeddel, ed.) (1990) or M. Krieger (1990), *Gene Transfer and Expression—A Laboratory Manual*, Stockton Press, New York, N.Y., and the references cited therein. Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993), *Current Opinion in Genetic and Development*, 3: 74–80, and the references cited therein provides an overview of the AAV life cycle. See also West et al. (1987), *Virology*, 160: 38–47; Carter et al. (1989), U.S. Pat. No. 4,797,368; Carter et al. (1993), WO 93/24641; Kotin (1994), *Human Gene Therapy*, 5: 793–801; Muzyczka (1994), *J. Clin. Invest.*, 94: 1351 and Samulski, supra, for an overview of AAV vectors.

Plasmids designed for producing recombinant vaccinia, such as pGS62, (Langford et. al. (1986), *Mol. Cell. Biol.*, 6: 3191–3199) may also be used. This plasmid consists of a cloning site for insertion of foreign nucleic acids, the P7.5 promoter of vaccinia to direct synthesis of the inserted nucleic acid, and the vaccinia TK gene flanking both ends of the foreign nucleic acid.

D. Insulin-Producing Cells Useful for Making the Engineered Cells Herein

A number of cell lines derived from pancreatic, β cells, commonly known as insulinoma cells, are useful for the practice of this invention and are readily available. For example, hamster insulinoma (HIT-T15) cells are well studied and are readily available from the American Type Tissue Collection. A number of rat insulinoma cell lines are also available. The RINm5F and RINr1046–38 cell lines were derived from a radiation induced tumor of the islet beta-cells (Gazdar et al., 1980; Clark et al., 1990). MSL-G2 cells were derived from a liver metastasis of an islet cell tumor. These cells require periodic passage in an animal host in order to maintain expression of their endogenous insulin gene (Madsen et al., 1988). Finally, the β-TC insulinoma cell line has been recently derived from transgenic animals injected with a T-antigen gene driven by an insulin promoter, resulting in specific expression of T-antigen in islet beta-cells and consequent immortalization of these cells (Efrat et al., 1988).

In addition, a number of insulin-secreting human cell lines have been reported. Habener et al. (1989), Factors that determine cell-specific gene expression in pancreatic endocrine tumor cells, Horm. Res. 32 (1–3): 61–6; Prentki M. and C. Wollheim (1984), Cytosolic free Ca2+ in insulin secreting cells and its regulation by isolated organelles, Experientia 40 (10): 1052–60; Kisanuki et al. (1995), Expression of insulin receptor on clonal pancreatic alpha cells and its possible role for insulin-stimulated negative regulation of glucagon secretion, Diabetologia 38(4): 422–9; Mogami et al. (1994), Inhibition of ATP-sensitive K+ channel by a non-sulfonylurea compound KAD-1229 in a pancreatic beta-cell line, MIN 6 cell, Eur. J. Pharmacol. 269(3): 293–8; Flatt et al. (1990), Stimulaory effects of glucagon-like peptides on human insulinoma cells and insulin-releasing clonal RINm5F cells, Diabetes Res. 13(2): 55–9.

In addition to cells that natively produce insulin, this invention also encompasses cells that express an exogenous insulin gene in addition to an exogenous calbindin gene. Such cells may be generated as described herein and by methods known in the art, using vectors that contain operably linked calbindin and insulin genes.

Any of the well known procedures for introducing foreign nucleotide sequences into host cells may be used. These include the use of calcium phosphate transduction, polybrene, protoplast fusion, electroporation, liposomes, DEAE dextran, receptor-mediated endocytosis, microinjection of the DNA directly into the cells, plasmid vectors, viral vectors and any of the other well known methods for introducing cloned genomic DNA, cDNA, synthetic DNA or other foreign nucleic acidic material into a host cell (see Sambrook et al., supra). It is only necessary that the particular genetic engineering procedure utilized be capable of successfully introducing at least one nucleic acid into the host cell which is capable of expressing the calbindin.

The culture of cells such as those used in conjunction with the present invention is well known in the art. Freshney (1994) CULTURE OF ANIMAL CELLS, A MANUAL OF BASIC TECHNIQUE, third edition, Wiley-Liss, New York, Kuchler et al. (1977), BIOCHEMICAL METHODS IN CELL CULTURE AND VIROLOGY, Kuchler, R. J., Dowden, Hutchinson and Ross, Inc., and the references cited therein provide a general guide to the culture of cells. Cultured cell systems often will be in the form of monolayers of cells, although cell suspensions are also used.

E. Analysis of Expression of Calbindin and Insulin in Engineered Cells

After a given cell is transduced with a nucleic acid construct that encodes a calbindin and optionally a drug sensitivity gene, it is important to detect which cells and cell lines express calbindin and to assess the level of expression of calbindin, insulin, and the drug sensitivity gene in engineered cells. This requires the detection of nucleic acids that encode a calbindin or insulin or the drug sensitivity, and also the detection of the protein gene products.

Nucleic acids and proteins are detected and quantified herein by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

1. Detection of Nucleic Acids Encoding Calbindin and Insulin

A variety of methods of specific DNA and RNA measurements and nucleic acid hybridization techniques known to those of skill in the art are useful for detecting and quantifying the presence and expression of calbindin, drug resistance genes, or insulin. For example, one method for evaluating the presence or and levels of calbindin DNA and calbindin expression in a sample involves a Southern transfer. Southern et al. (1975), *J. Mol. Biol.*, 98: 503. Briefly, the digested genomic DNA is run on agarose slab gels in buffer and transferred to membranes. Hybridization is carried out using probes that recognize a calbindin or an insulin sequence.

Similarly, a Northern transfer may be used for the detection of calbindin or insulin mRNA in samples of RNA from engineered insulin-producing cells that express the calbindin gene. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of a calbindin or an insulin transcript.

The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987), U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990), C&EN 36–47; *The Journal Of NIH Research* (1991), 3: 81–94; (Kwoh et al. (1989), *Proc. Natl. Acad. Sci. USA*, 86: 1173; Guatelli et al. (1990), *Proc. Natl. Acad. Sci. USA*, 87: 1874; Lomell et al. (1989), *J. Clin. Chem.*, 35: 1826; Landegren et al. (1988), *Science*, 241: 1077–1080; Van Brunt (1990), *Biotechnology*, 8: 291–294; Wu and Wallace (1989), *Gene*, 4: 560; Barringer et al. (1990), *Gene*, 89: 117, and Sooknanan and Malek (1995), *Biotechnology*, 13: 563–564. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in vitro amplification methods, for use as gene probes, or as inhibitor components are typically synthesized chemically according to the solid phase phosphoramidite triester method described by Beaucage and Caruthers (1981), *Tetrahedron Letts.*, 22(20): 1859–1862, e.g., using an automated synthesizer, as described in Needham-VanDevanter etal. (1984), *Nucleic Acids Res.*, 12: 6159–6168. Purification of oligonucleotides, where necessary, is typically performed by either native acrylamide gel electrophoresis or by anion-exchange HPLC as described in Pearson and Regnier (1983), *J. Chrom.*, 255: 137–149. The sequence of the synthetic oligonucleotides can be verified using the chemical degradation method of Maxam and Gilbert (1980) in Grossman and Moldave (eds.) Academic Press, New York, *Methods in Enzymology*, 65: 499–560.

An alternative means for determining the level of expression of calbindin is in situ hybridization. In situ hybridization assays are well known and are generally described in Angerer et al. (1987), *Methods Enzymol.*, 152: 649–660. In an in situ hybridization assay cells are fixed to a solid support, typically a glass slide. If DNA is to be probed, the cells are denatured with heat or alkali. The cells are then contacted with a hybridization solution at a moderate temperature to permit annealing of calbindin-specific probes that are labelled.

The probes are preferably labelled with radioisotopes or fluorescent reporters.

2. Detection of Calbindin and Insulin

The expression of calbindin or insulin may be detected or quantified by a variety of methods. Preferred methods involve the use of specific antibodies.

Methods of producing polyclonal and monoclonal antibodies are known to those of skill in the art. See, e.g., Coligan (1991), CURRENT PROTOCOLS IN IMMUNOLOGY, Wiley/Greene, N.Y.; and Harlow and Lane (1989), ANTIBODIES: A LABORATORY MANUAL, Cold Spring Harbor Press, N.Y.; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature*, 256: 495–497. Such techniques include antibody preparation by selection of antibodies from libraries of recombinant antibodies in phage or similar vectors. See, Huse et al. (1989), *Science*, 246: 1275–1281; and Ward etal. (1989), *Nature*, 341: 544–546. Specific monoclonal and polyclonal antibodies and antisera will usually bind with a $K_D$ of at least about 0.1 mM, more usually at least about 1 µM, preferably at least about 0.1 µM or better, and most typically and preferably, 0.01 µM or better.

The presence of a calbindin or insulin polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

F. Calbindin-expressing Artificial Tissue that Secretes Insulin in a Glucose-sensitive Fashion In other embodiments, the present invention is directed to methods of providing a glucose-responsive insulin-secreting capability to a mammal in need of such capability, such as an insulin-deficient mammal or a diabetic human. These methods generally comprise injecting or implanting into such a mammal engineered cells which secrete insulin in response to glucose.

Published techniques for the implantation of islets are applicable to implantation of cells engineered in accordance with the present invention. One such approach involves the encapsulation of engineered cells in a biocompatible coating that protects the encapsulated cells from immunological responses while allowing for the free diffusion of nutrients (including glucose), insulin and waste-products. The capsule also serves to prevent uncontrolled proliferation of the engineered cells.

A variety of cell encapsulation technologies have been developed that are applicable to the practice of the present invention (see, e.g., WO 9110470; WO 9110425; WO 9015637; WO 9002580; U.S. Pat. No. 5,011,472; U.S. Pat. No. 4,892,538; WO 8901967, each of the foregoing is incorporated by reference). The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

In general, encapsulation involves the polymerization of one or more matrix precursors in the presence of the cells to be encapsulated. The matrix precursors must be non-toxic, biocompatible, and must promote rapid polymerization. The term "polymerization", for the purposes of this application, is defined to include any reaction by which soluble precursor materials are transformed to a shape-retaining, insoluble form, including chain formation, increase in chain length, and covalent or non-covalent cross-linking.

Matrix precursors may include alginates, polylysine, chitosan plasma, fibrinogen, casein, fibrin, limulus lysate, milk protein, collagen, agarose, carrageenan, agar, guar gum, gum arabic, pectin, tragacanth gum, xanthan gum, and mixtures thereof. In general, a first aqueous solution containing matrix precursors is contacted with a second aqueous solution containing the cells. The concentration of matrix precursor for most matrices can be from 1 microgram/ml to 100 mg/ml, preferably from 50 microgram/ml to 20 mg/ml and optimally from 0.1 mg/ml to 6 mg/ml. The second solution may contain substances that promote polymerization, or these may be added in a third aqueous solution. Substances which promote polymerization may comprise multivalent ions in solution which can form a salt with matrix monomers. The optimum ion is a physiologically compatible ion such as calcium in a concentration which provides in the mixture of the first and second solution, a calcium ion concentration which promotes rapid polymerization of the gel polymer precursor.

Polymerization is allowed to proceed in a manner and for a time which yields a desired matrix shape, size, and porosity. The formed matrix particles can have a particle size as low as 0.02 mm in diameter and a size as large as 3 mm. Other ranges may be preferred and optimum for matrices having different matrix strengths, rigidity and different cell attachment characteristics.

For the production of spherical particles, the primary solution can be dripped or blown under air pressure into the secondary solution, the drop size being selected to yield the desired particle size. A distribution of particles can be obtained with certain gel precursors by subjecting the secondary mixture to agitation while the primary solution is rapidly poured into the secondary solution. Alternatively, the two solutions can be quickly mixed and the mixture placed in a cavity having the general configuration of the desired product.

Pore diameters range from $5 \times 10^{-3}$ to 40 microns, preferably from $2 \times 10^{-2}$ to 5 microns and optimally from 0.1 to 1 microns. The final porosity (average pore diameter, pore size distribution, average pore length, and total pore numbers) of the matrix particles is dependent upon the initial concentration of the gel polymer in the particle, the degree of gel polymer crosslinking obtained, the degree of spatial contraction occurring during matrix polymerization, and other variables, including processing temperatures. The matrix preferably has a porosity which allows only substances of molecular weight less than about 100,000 Daltons to pass transversely there-through while carrying blood along the length of the fiber. Substances of molecular weight below this cutoff, including substances which stimulate insulin secretion, such as glucose, amino acids, fatty acids, hormones (e.g., thyroxine, growth hormone, glucocorticoids), and neuronal stimuli diffuse through the hollow fiber wall to the islets. In response to these substances, the islets produce insulin, which diffuses through the matrix into the bloodstream.

The matrix can have any desired cell density. For pancreatic islet cells, the cell density can range from $10^3$ to $5 \times 10^8$ cells/ml of matrix.

Following polymerization, the formed matrix and enclosed cells are placed in a nutrient medium for maintaining the viability of the cells. The nutrients required for maintenance and propagation of various cells are generally well established and fully within the knowledge and skill of the person skilled in the art. For example, suitable media are described in READINGS IN MAMMALIAN CELL CULTURE, Robert Pollack (editor), Second edition New York: Cold Spring Harbor Laboratory (1981), and in other publications.

Further processing of the matrix to preserve or to expand or multiply the cells may be desirable, depending upon the cell type and factors involved in the insertion.

The cells embedded within matrix particles may be implanted in a mammal. The matrix is preferably implanted in a portion of the body which is not functionally affected by the implant and which will readily vascularize the implant. For example, pancreatic islet cells that are enclosed in a matrix can be implanted in the peritoneum, mesenteric omentum, kidney subcapsular space, splenic pulp, portal vein, and other sites appropriate for vascularization and function.

It is generally preferred that the implanted engineered cells of this invention remain encapsulated. In the event that cells escape from their capsules and invade other tissues, the fugitive cells may be destroyed by exposure to drugs to which the cells are sensitive. For example, the engineered cells of this invention may be manipulated to encode and express, constitutively or inducibly, a drug sensitivity gene such as cytosine deaminase. Any cells that escape their capsule may be exposed to 5-fluorocytosine, which is converted to the toxic metabolite 5 fluorouracil by fugitive cells and their offspring. The fugitive cells then die. Surrounding tissue cells that do not express the cytosine deaminase gene will not be killed.

In addition, unencapsulated glucose-sensitive cells of this invention may be implanted into a host animal. Implantation by this approach may circumvent problems with viability or function, at least for the short term, that may be encountered with the encapsulation strategy. This approach allows for testing of the function of the cells in experimental animals but is not preferred as a strategy for treating human patients.

G. Gene Therapy with Engineered Cells that Express Calbindin and Secrete Insulin in a Glucose-sensitive Fashion In one embodiment of the present invention, insulin-producing cells are taken from a mammal that does not secrete insulin in a glucose-sensitive fashion, optionally immortalized, transduced with a nucleic acid that encodes calbindin and, optionally, with a nucleic acid that encodes a drug sensitivity, and re-introduced into the mammal. This approach minimizes potential problems with immune rejection.

Pancreatic islet cells suitable for engineering and re-implantation can be derived from pancreatic tissue by numerous published procedures or they can be derived from tissue, organ or cell cultures. Procedures for preparing pancreas tissue for transplant are described by Lafferty et al. (1984), *Transplantation Proceedings* 14: 714 and by Lacy et al. (1984), *Ann. Rev. Immunol.* 2: 183. Briefly, pancreatic tissue is infused via the pancreatic duct with a solution of an enzyme such as collagenase which digests connective tissue and disrupts the integrity of the gland. The gland is further dissociated by shaking with marbles until tissue fragments are reduced to a size of less than 500 microns diameter. This disassociation procedure releases islets from the exocrine tissue that surrounded them. Islets are then separated from non-islet tissue by centrifugation on a discontinuous gradient such as one made of Ficoll TM (Pharmacia Fine Chemicals, Inc.) (27% w/v; 23.5% w/v; and 11% w/v). The difference in density of cell types to permit islets (lower density) to be positioned at the interface of the 11% and 23.5% Ficoll layers, while non islet tissue separated by centrifugation. Islets are collected, washed, and plated onto culture plates.

Primary isolates (or primary cultures) of islet cells in culture may be directly transduced as described above with vectors that contain a gene for calbindin and, optionally, a drug sensitivity gene, and implanted as described above. The cells to be implanted by the methods of the present invention can optionally be immortalized by a variety of techniques known in the art, which include transformation with Epstein-Barr virus or with retroviruses, or the transfection of oncogenes. For example, immortalization by Epstein-Barr virus may be employed, as described in U.S. Pat. No. 4,464,465, incorporated herein by reference. Epstein-Barr virus mutants which lack OriP and OriLyt origins of replication are particularly useful. Other useful method of immortalization are over-expression of a cellular gene for growth control such as c-myc as described by Bartlett etal. (1988), *Proc. Natl. Acad. Sci. USA*, 85: 3255–3259, or using the Rous sarcoma virus long terminal repeat-containing constructs, as described in U.S. Pat. No. 5,443,954, both incorporated herein by reference.

One possible source of pancreatic islet cells for implantation is fetal pancreatic proislet cells that are transduced with a nucleic acid that encodes a calbindin molecule. These can be derived from the recipient species (conspecific implantation) or they can be derived from a donor species which is different from the recipient species. When implanted into a suitable vascularized site in the body, the cells differentiate to produce islet cells in a vascularized environment, an artificial endocrine pancreas, which responds to serum glucose by producing and secreting insulin.

EXAMPLES

A. Example 1

Production of Glucose-sensitive Engineered Cells

Rat insulinoma cells (RIN) 1046–38) were transduced with pREP-calbindin-$D_{28k}$ and cloned as follows:

1. Materials $^{32}$P Deoxy-CTP (3000 Ci/mmol;3 70 MBq/ml) was purchased from Dupont-New England Nuclear Corp. (Boston, Mass.). Biotrans nylon membranes and olio (deoxythymidine)-cellulose were obtained from Boehringer Mannheim (Indianapolis, Ind.). Phenol, formamide and guanidinium isothiocyante were purchased from International Biotechnologies (New Haven, Conn.). Agarose (electrophoresis grade), the Random Primer DNA Labeling System and all restriction enzymes were obtained from BRL (Rockville, Md.). All other chemicals were of analytical grade.

2. Plasmids and Probes

Full length calbindin-$D_{28k}$ ($CaBP_{28k}$) cDNA (lacking the 5' and 3' untranslated region) is isolated by PCR from cDNA prepared from rat renal distal tubular mRNA. The PCR product is purified, digested with Not I and Sfi I and ligated into the eukaryotic expression vector pREP 4 (Invitrogen) downstream of the RSV promoter. The plasmids pFOXCAT1.SWT, pFOXCAT2.RIP1–85 and pFOXCAT2.RIP1–85.FF5 were kindly provided by Dr. M. German, University of California, San Francisco, Calif.

The CaBP probe for Northern analysis was a 17 bp fragment obtained by EcoR1 digestion of the Bluescript plasmid. The insulin probe was a 0.68 kb mouse insulin insert present in the PstI-EcoRI site of pGEM. The 2.1 kb chicken β-actin probe was a Hind III digest of pBR322 plasmid and the cDNA for 18S rRNA came from Ramareddy Guntaka (University of Missouri at Columbia).

3. Construction of a Vector for Expressing Calbindin in Islet Cells

Pancreatic islet cells are readily infectible by adenoviruses (Efrat et al., P.N.A.S. 92:6947,1995). Thus, an adenoviral vector is used to introduce calbindin into islet cells. A replication incompetent adenovirus vector expressing calbindin is constructed as follows.

A calbindin-encoding nucleic acid is cloned into a conventional plasmid such as bluescript, pgem, pUC or pBR322 as a carrier, together with (from 5' to 3):

I)

Bases 1–454 of Adenovirus type 5 (AD5) as found in GenBank X02996:
CATCATCAATAATATACCTTATTTTG-GATTGAAGCCAATATGATAATGAGGGG GTG-GAGTTTGTGACGTGGCGCGGGGCGTGG-GAACGGGGCGGGTGACGTAGTA
GTGTGGCGGAAGTGTGATGTTGCAAGT-GTGGCGGAACACATGTAAGCGACGG ATGTG-GCAAAAGTGACGTTTTGGTGTGCGCCG-GTGTACACAGGAAGTGACA
ATTTTCGCGCGGTTTTAGGCGGATGTTG-TAGTAAATTTGGGCGTAACCGAGTA AGATTTGGC-CATTTTCGCGGGAAAACTGAATAAGAG-GAAGTGAAATCTGAAT
AATTTTGTGTTACTCATAGCGCG-TAATATTTGTCTAGGGCCGCGGGGACTTTG
ACCGTTTACGTGGAGACTCGCCCAGGT-GTTTTTCTCAGGTGTTTTCCGCGTTC CGGGT-CAAAGTTGGCGTTTTATTATTATAGTCA

II)

The Cytomegalovirus immediate early enhancer nt 188–843 of M64943 as found in GenBank:
GGCACATGGCCAATGCATATCGATC-TATACATTGAATCAATATTGGCCATTAG CCATATT-AGTCATTGGTTATATAGCATAAAT-CAATATTGACTATTGGCCATTG
CATACGTTGTATCCATATCATAATATG-TACATTTATATTGGCTCATGTCCAATA TGACCGC-CATGTTGACATTGATTATTGACTAGT-TATTAATAGTAATCAATTAC
AGGGTCATTAGTTCATAGCCCATATATG-GAGTTCCGCGTTACATAACTTACGG TAAATGGC-CCGCCTGGCTGACCGCCCAACGAC-CCCCGCCCATTGACGTCAAT
AACGACGTATGTTCCCATAG-TAACGCTAATAGGGACTTTCCATTGACGTCAAT GGGAGGAGTATTTACGGTAAACTGC-CCACTTGGCAGTACATCAAGTGTATCAT ATGC-CAAGTACGCCCCCCATTGACGTCAAT-GACGGTAAATGGCCCGCCTGGC
ATTATGCCCAGTACATGACCTTACGG-GACTTTCCTACTTGGCAGTACATCTAC GTATTAGT-CATCACTATTACCATGGTGATGCG-GTTTTGGCAGTACATCAATGG
GTGTGGATAGCGGTTTGACTCACGGG-GATTTCCAAGTCTCCACCCCATTGACG TCAATGG-GAGTTTGTTTTGGCACCAAAATCAACGG-GACTTTCCAAAATGTCGT
AATAACTCCGCCCCATTGACG-CAAATGGGCGGTAGGCGTGTACAGTGGGAGG TCTATATAAGCAGAGCTCGTTTAGT-GAACCGTCAGATCGCCTGGAGACGCCA
TCCACGCTGTTTTGACCTCCATAGAAGA-CACCGGGACCGATCCAGCCTCCGC GGCCGG-GAACGGTGCATTGGAACGCGGATT

III)

A rat calbindin cDNA sequence containing a consensus Kozak Sequence as described in this application:
CCACCATGGCAGAATCCCACCTGCAGT-CATCTCTGATCACAGCCTCACAGTTT TTTGAGATCTGGCTTCATTTCGACGCT-
GATGGAAGTGGTTACCTGGAAGGAAA GGAGCTG-
CAGAACTTGATCCAGGAGCTTCTGCAG-
GCACGAAAGAAGGCTGGA
TTGGAGCTATCACCTGAGATGAAAAC-
CTTTGTGGATCAATATGGGCAGAGAG ATGATGG-
GAAAATAGGAATTGTAGAGTTGGCCCAT-
GTCTTACCCACCGAAGA
GAATTCCTGCTGCTCTTTCGATGCCAG-
CAACTGAAGTCCTGCGAGGAATTCA TGAAGACT-
TGGAGAAAGTATGACACTGACCACAGTG-
GCTTCATAGAAACGGA
GGAACTTAAGAACTTTCTTAAGGACCT-
GCTAGAGAAAGCAAACAAGACCGTG GATGATAC-
GAAACTTGCTGAGTACACAGACCTCAT-
GCTGAAGCTGTTCGACT
CAAATAATGATGGGAAGCTGGAGCTGA-
CAGAGATGGCCAGGTTACTACCAGT GCAG-
GAAAATTTCCTTCTTAAATTCCAGG-
GAATCAAAATGTGTGGGAAAGAG
TTCAATAAGGCTTTTGAGTTATATGAT-
CAGGATGGCAACGGATACATAGATGA AAAT-
GAGCTGGATGCCTTACTGAAAGACCTGT-
GTGAGAAAACAAACAGGAA
TTGGATATTAACAATATTTCTACATA-
CAAGAAGAACATAATGGCCTTGTCGGA TGGAGG-
GAAGCTGTACCGAACAGATCTTGCCCT-
TATTCTCTCTGCTGGGGACA ACTAG
IV)
An SV40 polyadenylation signal as found in nucleotides
2529–2668 of the SV40 genome (GenBank V01380)
TGGGGATCCAGACATGATAAGATACAT-
TGATGAGTTTGGACAAACCACAA CTAGAATG-
CAGTGAAAAAAATGCTTTATTTGT-
GAAATTTGTGATGCTATT
GCTTTATTTGTAACCATTATAAGCTG-
CAATAAACAAGTT
V)
Nucleotides 3334–6231 of Adenovirus type 5 (AD5) as
found in GenBank X02996:
GGAAGGTGCTGAGGTACGATGAGACCCG-
CACCAGGTGCAGACCCTGCGAGTG TGGCGGTAAA-
CATATTAGGAACCAGCCTGTGATGCTG-
GATGTGACCGAGGAG
CTGAGGCCCGATCACTTGGTGCTGGCCT-
GCACCCGCGCTGAGTTTGGCTCTAG CGATGAA-
GATACAGATTGAGGTACTGAAATGT-
GTGGGCGTGGCTTAAGGGTG
GGAAAGAATATATAAGGTGGGGGTCT-
TATGTAGTTTTGTATCTGTTTTGCAGC AGCCGC-
CGCCGCCATGAGCAC-
CAACTCGTTTGATGGAAGCATTGTGAGCTCA
TATTTGACAACGCGCATGC-
CCCCATGGGCCGGGGTGCGTCAGAATGTGATGG
GCTCCAGCATTGATGGTCGCCCCGTCCT-
GCCCGCAAACTCTACTACCTTGACC TACGAGAC-
CGTGTCTGGAACGCCGTTGGAGACTG-
CAGCCTCCGCCGCCGCTT
CAGCCGCTGCAGCCACCGCCCGCGGAT-
TGTGACTGACTTTGCTTTCCTGAGC CCGCTTG-
CAAGCAGTGCAGCTTCCCGTTCATCCGC-
CCGCGATGACAAGTTGA
CGGCTCTTTTGGCACAATTGGAT-
TCTTTGACCCGGGAACTTAATGTCGTTTCTC
AGCAGCTGTTGGATCTGCGCCAGCAG-
GTTTCTGCCCTGAAGGCTTCCTCCCCT CCCAAT-
GCGGTTTAAAACATAAATAAAAAACCA- GACTCTGTTTGGATTTGGAT
CAAGCAAGTGTCTTGCTGTCTTTATT-
TAGGGGTTTTGCGCGCGCGGTAGGCCC GGGAC-
CAGCGGTCTCGGTCGTTGAGGGTCCTGT-
GTATTTTTCCAGGACGTGG
TAAAGGTGACTCTGGATGTTCAGATA-
CATGGGCATAAGCCCGTCTCTGGGGTG GAGGTAG-
CACCACTGCAGAGCTTCATGCT-
GCGGGGTGGTGTTGTAGATGATC
CAGTCGTAGCAGGAGCGCTGGGCGTGGT-
GCCTAAAAATGTCTTTCAGTAGCA AGCTGATTGC-
CAGGGGCAGGCCCTTGGTGTAAGTGTT-
TACAAAGCGGTTAAG
CTGGGATGGGTGCATACGTGGGGATAT-
GAGATGCATCTTGGACTGTATTTTTA GGTTGGCTAT-
GTTCCAGCCATATCCCTCCGGGGAT-
TCATGTTGTGCAGAACC
ACCAGCACAGTGTATCCGGTGCACTTGG-
GAAATTTGTCATGTAGCTTAGAAGG AAATGCGTG-
GAAGAACTTGGAGACGCCCTTGTGAC-
CTCCAAGATTTTCCATG
CATTCGTCCATAATGATGGCAATGGGC-
CCACGGGCGGCGGCCTGGGCGAAGA TATTTCTGG-
GATCACTAACGTCATAGTTGTGTTCCAG-
GATGAGATCGTCATAG
GCCATTTTTACAAAGCGCGGGCG-
GAGGGTGCCAGACTGCGGTATAATGGTTC CATCCG-
GCCCAGGGGCGTAGTTACCCTCACA-
GATTTGCATTTCCACGCTTTG
AGTTCAGATGGGGGGATCATGTCTACCT-
GCGGGGCGATGAAGAAAACGGTTT CCGGGG-
TAGGGGAGATCAGCTGGGAAGAAAGCAG-
GTTCCTGAGCAGCTGCG
ACTTACCGCAGCCGGTGGGCCCGTAAAT-
CACACCTATTACCGGGTGCAACTG GTAGTTAA-
GAGAGCTGCAGCTGCCGTCATCCCTGAG-
CAGGGGGGCCACTTCG
TTAAGCATGTCCCTGACTCGCAT-
GTTTTCCCTGACCAAATCCGCCAGAAGGCG
CTCGCCGCCCAGCGATAGCAGTTCTTG-
CAAGGAAGCAAAGTTTTTCAACGGTT TGAGAC-
CGTCCGCCGTAGGCAT-
GCTTTTGAGCGTTTGACCAAGCAGTTCCAGG
CGGTCCCACAGCTCGGTCACCTGCTC-
TACGGCATCTCGATCCAGCATATCTCC
TCGTTTCGCGGGTTGGGGCG-
GCTTTCGCTGTACGGCAGTAGTCGGTGCTCGTC
CAGACGGGCCAGGGTCATGTCTTTC-
CACGGGCGCAGGGTCCTCGTCAGCGTA
GTCTGGGTCACGGTGAAGGGGTGCGCTC-
CGGGCTGCGCGCTGGCCAGGGTGC GCTTGAG-
GCTGGTCCTGCTGGTGCTGAAGCGCTGC-
CGGTCTTCGCCCTGCGCG
TCGGCCAGGTAGCATTTGACCATGGTGT-
CATAGTCCAGCCCCTCCGCGGCGTG GCCCTTG-
GCGCGCAGCTTGCCCTTGGAGGAGCGC-
CGCACGAGGGGCAGTGC
AGACTTTTGAGGGCGTAGAGCT-
TGGGCGCGAGAAATACCGATTCCGGGGAGT
AGGCATCCGCGCCGCAGGCCCCGCA-
GACGGTCTCGCATTCCACGAGCCAGGT
GAGCTCTGGCCGTTCGGGGTCAAAAAC-
CAGGTTTCCCCCATGCTTTTTGATGC GTTTCTTAC-
CTCTGGTTTCCATGAGCCGGTGTC-
CACGCTCGGTGACGAAAAGG
CTGTCCGTGTCCCCGTATACAGACT-
TGAGAGGCCTGTCCTCGAGCGGTGTTCC GCGGTC- CTCCTCGTATAGAAACTCGGACCACTCT-
GAGACAAAGGCTCGCGTC
CAGGCCAGCACGAAGGAGGCTAAGTGG-
GAGGGGTAGCGGTCGTTGTCCACTA GGGGGTC-
CACTCGCTCCAGGGTGTGAAGACACAT-
GTCGCCCTCTTCGGCATC
AAGGAAGGTGATTGGTTTGTAGGTGTAG-
GCCACGTGACCGGGTGTTCCTGAA GGGGGGC-
TATAAAAGGGGGTGGGGGCGCGTTCGTC-
CTCACTCTCTTCCGCAT
CGCTGTCTGCGAGGGCCAGCTGT-
TGGGGTGAGTACTCCCTCTGAAAAGCGGG CAT-
GACTTCTGCGCTAAGATTGTCAGTTTC-
CAAAAACGAGGAGGATTTGATAT
TCACCTGGCCCGCGGTGATGC-
CTTTGAGGGTGGCCGCATCCATCTGGTCAGA AAA-
GACAATCTT Sequences I–V are operably linked in the prescribed order by suitable restriction and ligation reactions. Together, these comprise a calbindin-adenovirus 5 shuttle vector.

5 micrograms of the adenovirus-calbindin shuttle vector described above and one microgram of the right arm of Adenovirus 5 or its variants (either the large XbaI fragment of Adenovirus dl309, adenovirus dl327 or nucleotides 3334 to the rightmost end of adenovirus 5) are co-transfected into HEK 293 cells using calcium phosphate transfection. The cells are overlaid with soft agarose and after 5–8 days, individual lytic plaques identified by inspection after neutral red staining. The agarose plugs containing viruses are picked, expanded and virus is prepared by infecting HEK 293 cells and purifying virus by CsCI banding.

4. Construction of a Bicistronic Expression Cassette Expressing Calbindin (D28K) and the Herpes Simplex Virus Thymidine Kinase Three nucleic acid fragments are cloned into the pREP4 (Invitrogen) expression vector to yield a bicistronic expression cassette expressing both calbindin (D28K) and the Herpes Simplex Virus thymidine kinase.

The first fragment is the coding region of the Herpes Simplex Virus thymidine kinase gene (GenBank accession number: V00467; M. J. Wagner, J. A. Sharp & W. C. Summers (1981), *Proc. Nat'l. Acad. Sci. USA*, 78: 1441–5) in which an NcoI restriction site is placed on the 5' end (PCR primer is 5'gatcaCCatggcttcgtaccccctgcc) and a BamHI site on the 3' end (PCR primer is acgtaGGATCccaacacgatgtttgtgc) using a PCR. Fragment 2 is the IRES fragment from the encephalomyocarditis virus which is obtained from the commercially available plasmid pCITE-1 (Novagen) by PCR. An XhoI site is placed on the 5' end of the IRES fragment by PCR (primer is ctagctcgagCAATTCCGCCCCTCTCC) and the 3' NcoI site is preserved using the 3' PCR primer (gcatCCATGGTATTATCGTGTTTTTC). Fragment 3 is the calbindin cDNA which is modified by PCR to have a HindIII site on its 5' end along with a KOZAK consensus sequence, and a NotI site on its 3' end. The 5' PCR primer used is agctaagcttCCACCatggcagaatcccacctg, and the 3' PCR primer used is ACTCGCGGCCGCctagttgtccccagcagag.

The vector pREP4 is digested with XhoI and BamHI. The HSV-Tk gene (fragment 1) is digested with BamHI and NcoI. The IRES fragment (fragment 2) is digested with XhoI and NcoI. These fragments are combined in a standard trimolecular ligation to yield an intermediate plasmid designated pREP4-IRES-tk.

The intermediate plasmid pREP4-IRES-tk is digested with HindIII and NotI. Fragment 3 containing the calbindin gene is digested with HindIII and NotI. These are ligated together to yield the plasmid pREP4-CB-IRES-tk.

5. Stable Transduction of RIN 1046–38 Cells and Clonal Selection

About 50% confluent RIN 1046–38 cells (grown in RPMI 1640) in T-75 flasks are used to carry out stable transduction by lipofection. 10 $\mu$g each of pREP 4 (vector alone) and pREP-CaBP$_{28k}$ (calbindin over-expressing) or pREP4-CB-IRES-tk are mixed well in separate tubes with 50 to 75 $\mu$l of lipofectin and this mixture is added to the cells (in 5 ml of serum-free media) and incubated for 18 h at 37° C. Media with serum is added to the cells the next day. On the third day after transduction, media containing the selection antibiotic hygromycin (400 $\mu$g/ml) is added to the cells. From this point onwards, cell death occurs. The surviving cells in about 3–4 weeks develop into colonies of cells. Each colony is handpicked under sterile conditions and propagated in 24-well plates. When each well is sufficiently confluent with cells, that clone is further expanded serially in 6-well plates and then in T-25 flasks.

6. Western Analysis and Radioimmunoassay

In order to determine if any clones overexpress calbindin, a Western blot analysis is done. Cell extracts of various clones are prepared by freeze-thawing the cells in 50 mM Tris-HCl buffer, pH 7.8. The cell extract is heat treated at 65° C. for 10 min. and then microfuged at 14,000 g for 10 min. at 4° C. The supernatant is then used for protein estimation using the Bio-Rad reagent. 5 $\mu$g protein of each clone was used for electrophoresis on a 15% SDS-PAGE gel. The proteins are then transferred onto an Immobilon-P membrane, the membrane was blocked using 2% BSA in 1xPBS and a 1:4 dilution of normal goat antisera in 2% BSA/PBS. After washing the membrane with PBS, the membrane is incubated with rabbit anti-rat calbindin antisera overnight at 4° C. with $^{125}$I-labeled protein A/2% BSA/PRS/ 0.05% Tween-20, then washed thoroughly with PBS and air dried before autoradiographic exposure.

Calbindin levels are determined by radioimmunoassay (RIA) using antiserum against rat renal calbindin and using rat renal CaBP as standard (Sonnenberg et al., 1984).

7. mRNA Isolation and Northern Analysis

Total RNA was isolated from various clones by the guanidinium isothiocyanate/phenol/chloroform method (Chomzynski and Sacchi (1987), Single step method of RNA isolation by acid guanidinium thiocyanate-phenol-chloroform extraction. Anal. Biochem. 162: 15–159) and poly(A)+RNA was selected via oligo(dT) cellulose affinity chromatography. Equivalent amounts poly(A)+RNA were separated under denaturing conditions on a 1.2% formaldehyde agarose gel and transferred to a nylon filter in 20% SSC. The filters were baked at 80° C. for 2–3 h, prehybridized, hybridized and washed using 1–3x10$^6$ cpm/ml 32P labeled cDNA/filter. cDNA was labeled to a specific activity of 10$^8$–10$^9$ cpm/$\mu$g DNA by the oligonucleotide labeling procedure using random primed DNA labeling kit (Boehringer-Mannheim). After probing with calbindin-D$_{28k}$ cDNA, the filters were probed with insulin, $\beta$-actin and 18S cDNA after stripping using a solution that contained 50% formamide, 6xSSC at 65° C./30 min. between each probing.

8. Insulin Secretion Assays and Insulin Content

Five positive clones were found to overexpress calbindin as determined by Western blot analysis (FIG. 1). The positive clones were the ones numbered C2, C10, C11, C13 and C5. The clones were plated in 12-well plates with 2–3x10$^5$ cells/well and after 2–4 days of culture, the medium was removed. Fresh media was added to the culture and incubated for 1 h before collecting samples for insulin assay. Insulin was determined by RIA with a dextran-charcoal method using a rat insulin standard (Novo Laboratories, Danbury, Connecticut) and guinea pig anti-insulin serum (Clark, 1990). $^{125}$I labeled insulin was obtained from DuPont-New England Nuclear. To determine insulin content of clones, cells were plated as for secretion studies and after two days cells were rinsed with PBS, acid-ethanol with 50 mM benzamidine was added to the wells (0.5 ml) and the wells were sealed with pressure sensitive film. The extract was collected after 48 h at 4° C. diluted >10 times with assay buffer, then frozen at −20° C. for subsequent insulin assays.

Levels of calbindin-$D_{28k}$ as measured by radioimmunoassay in the positive clones overexpressing calbindin are shown in Table I.

TABLE I

Levels of Calbindin-$D_{28k}$ in Selected Transfected RIN Cells as Determined by Radioimmunoassay

| | Calbindin-$D_{28k}$ (pg/mg protein) | Fold induction |
|---|---|---|
| Control (transfected with vector alone) | 0.4 ± 0.1 | |
| $C_2$ | 14.2 ± 1.7 | 35.0 |
| $C_{10}$ | 3.7 ± 0.4 | 9.0 |
| $C_{13}$ | 3.3 ± 0.1 | 8.0 |
| $C_5$ | 3.2 ± 0.6 | 7.8 |
| $C_{11}$ | 2.5 ± 0.2 | 6.5 |

The average concentration of calbindin in cells transduced with vector alone was 0.4±0.1 μg/mg protein. Clone C2 expressed the highest level of calbindin (14.2±1.7 μg/mg protein) which represented a 35 fold induction in calbindin. Clone C10 expressed the next highest level of calbindin (3.7±0.4 μg/mg protein) followed by C13, C5 and C11. Thus, as shown in Table I, positive clones were found to overexpress calbindin from 6.5 fold (for C11) to a higher level of overexpression of 35 fold for C2.

Figure 2:
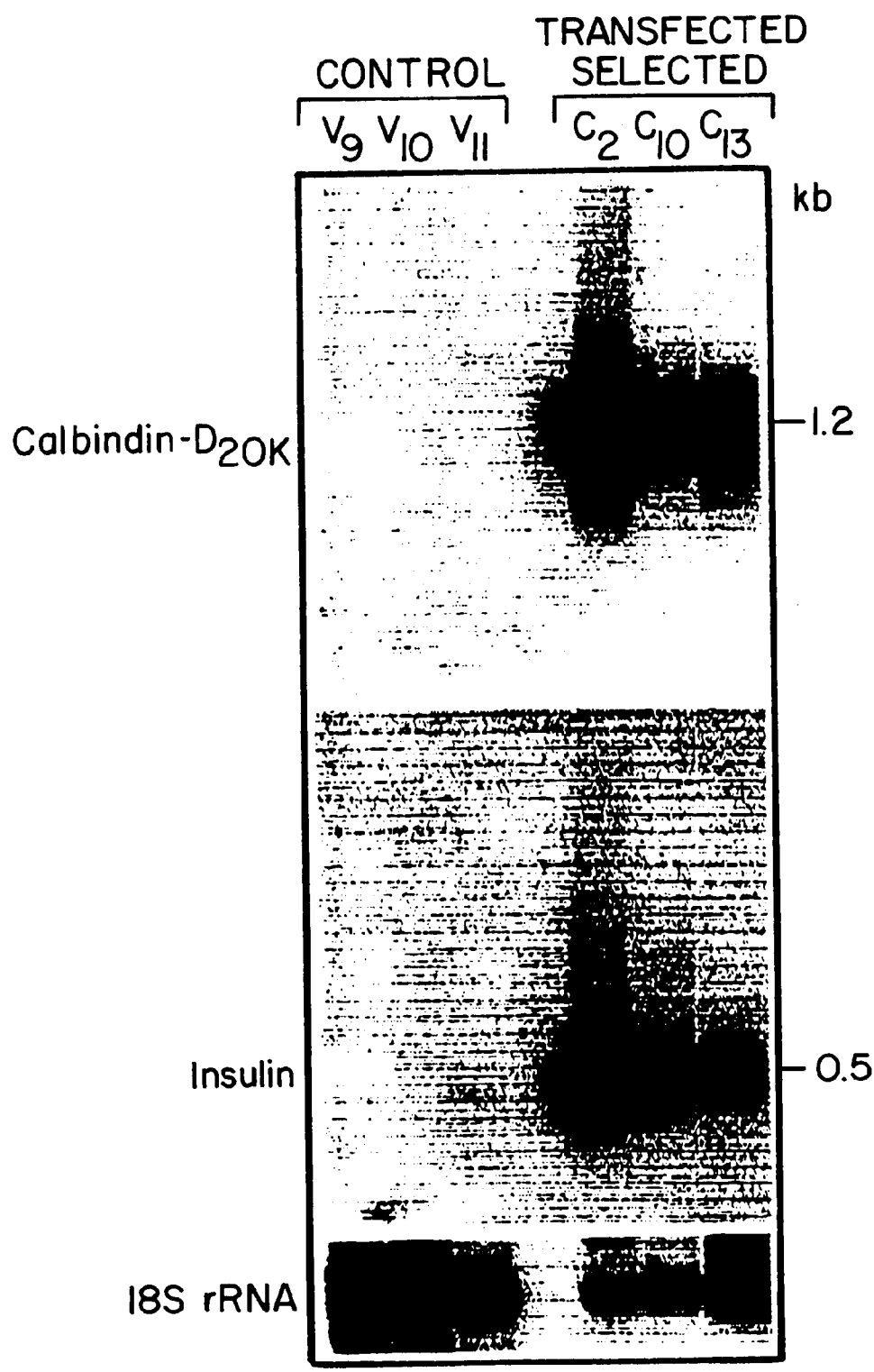
FIG. 2. Northern blot analyses of calbindin-$D_{28k}$ and insulin mRNA in RIN cells transformed with pREP-calbindin-$D_{28}$.

Results of Northern blot analyses indicated an increase in calbindin-$D_{28k}$ and insulin mRNA in RIN cells transduced with pREP-calbindin-$D_{28k}$ (FIG. 2). The insulin results are also summarized in Table II.

TABLE II

INSULIN SECRETION

| | Insulin (ng/$10^6$ cells) | Fold Induction |
|---|---|---|
| Control (transfected with vector alone) | 0.14 ± 0.02 | |
| $C_2$ | 5.46 ± 0.66 | 39.0 |
| $C_{10}$ | 0.73 ± 0.07 | 5.6 |

Similar to the results observed for calbindin protein, the most abundant levels of calbindin-$D_{28k}$ and insulin mRNA were found in clone C2. High levels were found in clone C10 and C13. Clone C11 which was found to contain the least amount of calbindin-$D_{28k}$ mRNA. Thus, Northern analyses revealed increases in abundance in calbindin and insulin mRNA similar to those observed for calbindin protein. As shown in Table II, transduction and overexpression of calbindin in RIN cells resulted in not only increased biosynthesis, but also increased secretion of insulin.

Figure 3:
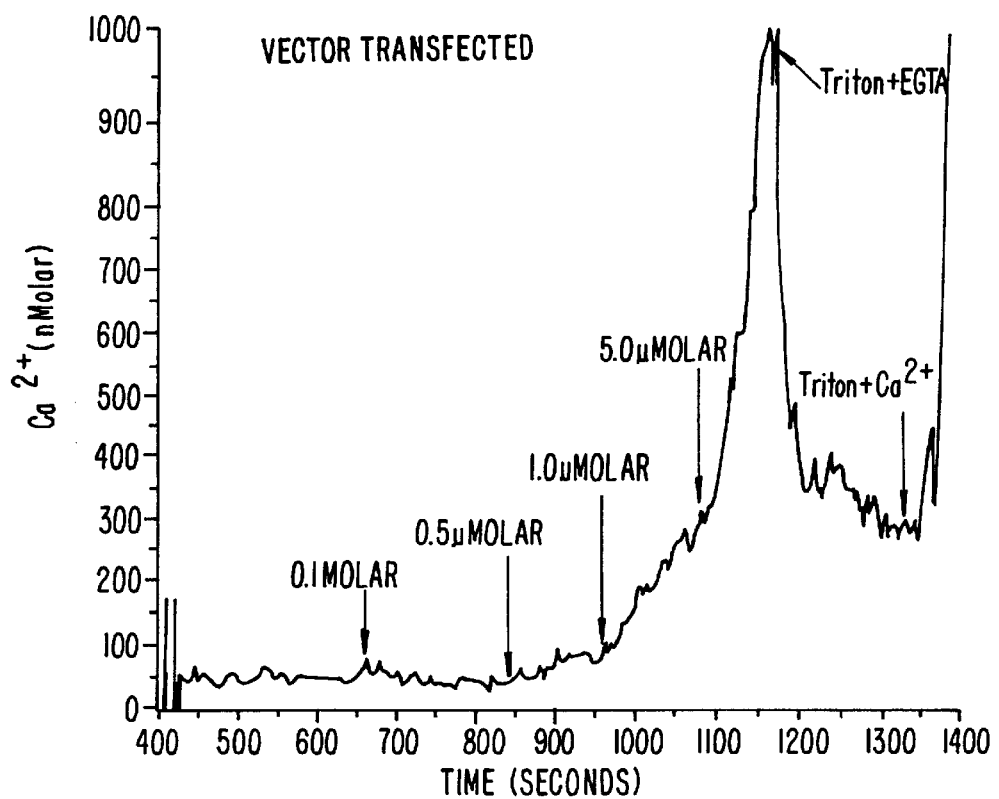
FIG. 3. Changes in intracellular calcium in response to calcium ionophore A23187.
Figure 3:
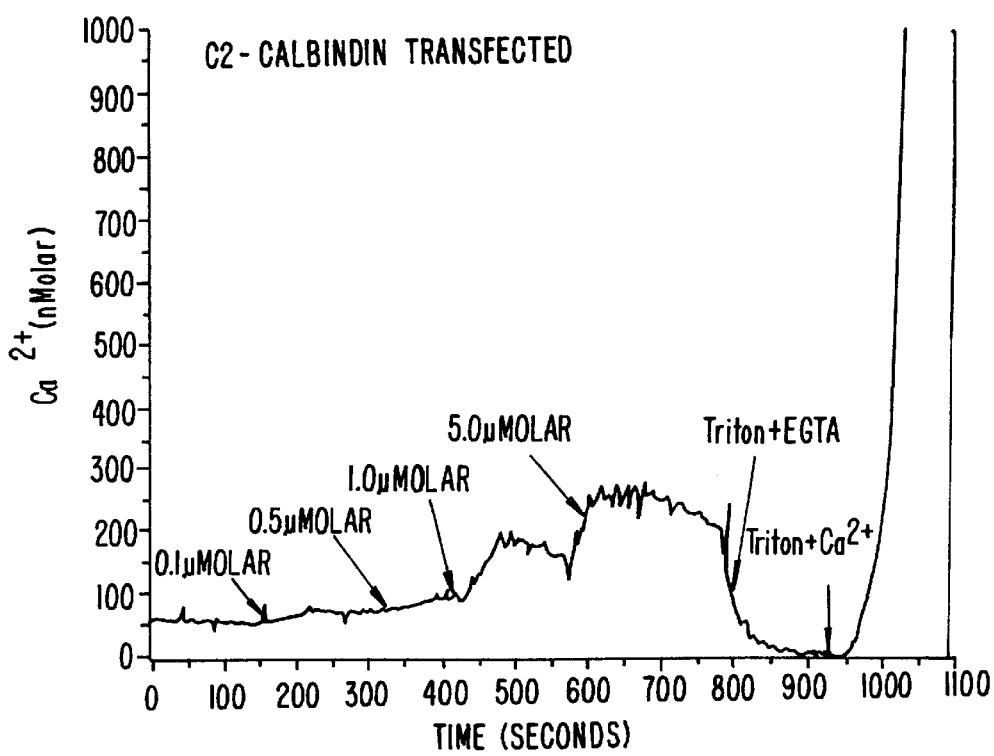

In order to determine the mechanism whereby overexpression of calbindin results in increased insulin biosynthesis and secretion, intracellular calcium levels were examined. In control cells, there was a significantly greater increase in intracellular calcium ($p<0.05$) in response to calcium ionophore A23187 (1–5 μM) when compared to changes in intracellular calcium in RIN cells overexpressing calbindin and treated with the same concentration of ionophore (FIG. 3). Whether the modification of intracellular calcium by calbindin is related to the insulin secretory process remains to be determined. Although the exact mechanism is not clear at this time, our findings do suggest a significant role for calbindin-$D_{28k}$ in the induction of insulin secretion and expression.

B. Example 2

Engineered Human Cell Line that Expresses Calbindin

An engineered calbindin-expressing human cell obtained as described in Madsen et al., (1991), Islet amyloid polypeptide and insulin expression are controlled differently in primary and transformed islet cells, Mol Endocrinol 5(1): 143–8 and Flatt et al. (1990), Stimulatory effects of glucagon-like peptides on human insulinoma cells and insulin-releasing clonal RINm5F cells, Diabetes Res. 13(2): 55–9., is generated using human insulin producing cells and the methods described in example 1.

C. Example 3

Construction and Use of Artificial Tissue Comprising Engineered Calbindin-expressing Glucose-sensitive Cells The engineered cells of the present invention are implanted, for example, using the alginate-polylysine encapsulation technique of O'Shea and Sun (1986), Diabetes 35: 943–946, as modified by Fritschy et al. (1991), Diabetes 40: 37.

Monolayers of cultured engineered calbindin-expressing insulinoma cells are harvested by trypsinization and washed twice in isotonic, neutral pH buffer. The number of cells and the percent viability are determined by trypan blue exclusion with a hemocytometer. Viable cells are maintained on ice and centrifuged (1500×g) for 5 min before use, and the supernatant is discarded.

The collected engineered cells are suspended in 0.1–1.3% sodium alginate and encapsulated by extrusion of drops of the cell/alginate suspension through a syringe into $CaCl_2$. After several washing steps, the droplets are suspended in 0.1–3% polylysine or chitosan and rewashed. The alginate within the capsules is then reliquified by suspension in 1 mM EGTA and then rewashed with Krebs balanced salt buffer. Each capsule contains several hundred cells and has a diameter of approximately 1 mm.

Alternatively about one gram of calcium sodium alginate (Kelcosol™, Kelco Corp.) is wrapped in aluminum foil and autoclaved for 15 minutes. A 1% solution of calcium sodium alginate in cell culture medium is prepared at 35–40° C. In a separate culture tube, about $10^8$ engineered cells are pelleted by gentle centrifugation. The culture medium is decanted from the pelleted islets and approximately 14 ml of the alginate/medium solution is added. After gently mixing the cells with alginate/medium solution to form a homogeneous mixture, the cell mixture is centrifuged at about 5000×g for five minutes to form two layers. The bottom layer contains a viscous alginate and cell suspension and the top layer consists of the culture medium. The culture medium is removed by pipetting, and the remaining encapsulated cell suspension is transferred to a syringe.

The encapsulated cells are injected intraperitoneally into a suitable recipient that has an impaired ability to secrete insulin in a glucose-sensitive fashion. The blood glucose levels of the recipient are monitored by methods known in the art to ensure that glucose homeostasis is maintained.

The total number of cells to be implanted in a given recipient vary as a function of the recipient's body mass, metabolic needs, innate ability to secrete insulin and innate ability to control glucose. In general, the number of implanted cells should be sufficient to maintain glucose homeostasis. The accumulated data from human and animal experiments indicates that the number of islets generally required to compensate for impaired insulin secretion is about 5,000 islets/kg body weight. Thus, a 70 kg patient would need approximately 350,000 islets to maintain suitable blood glucose levels, or between about $10^5$ and about $10^{10}$ encapsulated cells.

We claim:

1. An engineered cell that secretes insulin in a glucose-sensitive fashion and that expresses a drug sensitivity, wherein said cell expresses a first exogenous nucleic acid that encodes a calbindin molecule and a second exogenous nucleic acid that encodes a drug sensitivity, with the proviso that in the absence of said first exogenous nucleic acid that encodes a calbindin molecule, the host cell does not secrete insulin in glucose-sensitive fashion.

2. A cell according to claim 1, wherein said insulin secreting cell is selected from the group consisting of a primary isolate, or an insulinoma.

3. An engineered cell that secretes insulin in a glucose-sensitive fashion, wherein said cell expresses an exogenous nucleic acid that encodes a calbindin molecule, with the proviso that in the absence of said first exogenous nucleic acid that encodes a calbindin molecule, the host cell does not secrete insulin in glucose-sensitive fashion, and with the additional proviso that the host cell may not be a rat insulinoma cell.

4. A method for imparting glucose-sensitive insulin secretion to a host cell that does not exhibit glucose-sensitive insulin secretion, comprising the steps of:
 a) providing a cell that is capable of producing and secreting insulin, but has an impaired ability to secrete insulin in a glucose sensitive fashion;
 b) stably transducing said cell with a nucleic acid that encodes a calbindin molecule and optionally with a nucleic acid that encodes a drug sensitivity, wherein the expression of said nucleic acid that encodes a calbindin molecule imparts to the engineered cell the enhanced ability to secrete insulin in a glucose-sensitive fashion.

5. A method according to claim 4, wherein said cell is selected from the group consisting of a primary isolate, or an insulinoma.

6. A method of treating a mammal having an impaired ability to secrete insulin in response to glucose, comprising stably introducing into said mammal an engineered cell that expresses an exogenous nucleic acid that encodes a calbindin molecule, wherein said expression of said exogenous nucleic acid that encodes a calbindin molecule imparts to the engineered cell line the enhanced ability to secrete insulin in glucose-sensitive fashion.

7. A method according to claim 6, wherein said mammal is a human patient.

8. A method according to claim 6, wherein said cell is conspecific with the mammal into which it is stably introduced.

9. A method according to claim 6, wherein said cell is syngeneic with the mammal into which it is stably introduced.

10. A method according to claim 6, wherein said cell is an insulinoma cell line.

11. A method according to claim 6, comprising the steps of:
  a) stably transducing an insulin-secreting cell with a nucleic acid that encodes a calbindin molecule and optionally with a second nucleic acid that encodes a drug sensitivity, wherein the expression of said nucleic acid that encodes a calbindin molecule imparts to said engineered cell the enhanced ability to secrete insulin in a glucose sensitive fashion;
  b) selecting an engineered cell that secretes insulin in a glucose-sensitive fashion, and
  c) stably introducing into a mammal said engineered cell that secretes insulin in a glucose-sensitive fashion.

12. A method according to claim 11, wherein said cell that is capable of producing and secreting insulin but does not secrete insulin in a glucose-sensitive fashion is selected from the group consisting of a primary isolate, or an insulinoma.

13. A composition comprising
  a) an engineered cell that secretes insulin in a glucose-sensitive fashion, wherein said cell expresses an exogenous nucleic acid that encodes a calbindin molecule, with the proviso that in the absence of said exogenous nucleic acid that encodes a calbindin molecule, the host cell does not secrete insulin in glucose-sensitive fashion, and
  b) a semipermeable composition that encloses the engineered cell.

14. A composition according to claim 13, wherein the semipermeable composition that encloses the engineered cell is a porous matrix made of a non-toxic biocompatible polymer, wherein the pore structure and size of the matrix permits the diffusion of glucose and nutrients into the matrix, and the diffusion of insulin and waste products out of the matrix.

15. The composition of claim 13 wherein the matrix is produced by
  (a) polymerizing polymer precursors in an aqueous solution containing matrix polymer precursors and viable engineered cells, to form a shape-retaining solid matrix comprising viable cells, matrix polymer and reversible gel polymer,
  (b) removing unpolymerized gel precursors from the matrix, and wherein the conditions and reagents are selected to not significantly impair the viability of the cells.

16. The composition of claim 13, wherein the matrix polymer precursor is selected from the group consisting of plasma, fibrinogen, casein, fibrin, limulus lysate, milk protein, collagen, agarose, carrageenan, agar, alginate, guar gum, gum arabic, pectin, tragacanth gum, xanthan gum, and mixtures thereof.

17. A composition according to claim 13, wherein said engineered cell is selected from the group consisting of an engineered primary isolate, or an insulinoma.

18. A composition of claim 13 wherein said composition is stably maintained in a mammal, such that glucose from the mammal's biological fluids contacts the engineered cell within the matrix and stimulate glucose-sensitive insulin secretion, and such that the insulin secreted in response to glucose enters into the mammals' bloodstream.

19. A composition according to claim 18 wherein said mammal is a human patient.

* * * * *

UNITED STATES PATENT AND TRADEMARK OFFICE
CERTIFICATE OF CORRECTION

PATENT NO. : 6,319,495 B1
DATED : November 20, 2001
INVENTOR(S) : Pollock et al.

It is certified that error appears in the above-identified patent and that said Letters Patent is hereby corrected as shown below:

Columns 37-40,
Beginning at line 52, please delete claims 1-19 and insert therefor following:
-- 1. An engineered beta-cell that naturally secretes insulin and that expresses a cytotoxic selectable marker, wherein said beta-cell expresses a first exogenous nucleic acid that encodes a calbindin molecule and a second exogenous nucleic acid that encodes the cytotoxic selectable marker.

2. A beta-cell according to claim 1, wherein said insulin secreting beta-cell is selected from the group consisting of a primary isolate, or an insulinoma.

3. An engineered beta-cell that naturally secretes insulin wherein said beta-cell expresses an exogenous nucleic acid that encodes a calbindin molecule, and wherein the beta-cell is not a rat insulinoma cell.

4. A method for generating an engineered insulin-secreting beta-cell that expresses exogenous calbindin comprising the steps of:
 a) providing a beta-cell that naturally secretes insulin;
 b) stably transducing said beta-cell with a nucleic acid that encodes a calbindin molecule and optionally with a nucleic acid that encodes a cytotoxic selectable marker.

5. A method according to claim 4, wherein said beta-cell is selected from the group consisting of a primary isolate, or an insulinoma.

6. A method of treating a mammal having an impaired ability to secrete insulin, comprising stably introducing into said mammal an engineered beta-cell that naturally secretes insulin and expresses an exogenous nucleic acid that encodes a calbindin molecule.

7. A method according to claim 6, wherein said mammal is a human patient.

8. A method according to claim 6, wherein said beta-cell is conspecific with the mammal into which it is stably introduced.

9. A method according to claim 6, wherein said beta-cell is syngeneic with the mammal into which it is stably introduced.

10. A method according to claim 6, wherein said beta-cell is an insulinoma cell line.

UNITED STATES PATENT AND TRADEMARK OFFICE
CERTIFICATE OF CORRECTION

PATENT NO. : 6,319,495 B1
DATED : November 20, 2001
INVENTOR(S) : Pollock et al.

It is certified that error appears in the above-identified patent and that said Letters Patent is hereby corrected as shown below:

11. A method according to claim 6, comprising the steps of:
 a) stably transducing an insulin-secreting beta-cell with a nucleic acid that encodes a calbindin molecule and optionally with a second nucleic acid that encodes a cytotoxic selectable marker.
 and
 b) stably introducing into a mammal said engineered beta-cell that secretes insulin and expresses exogenous calbindin.

12. A method according to claim 11, wherein said beta-cell that secretes insulin is selected from the group consisting of a primary isolate, or an insulinoma.

13. A composition comprising
 a) an engineered beta-cell that naturally secretes insulin, wherein said beta-cell expresses an exogenous nucleic acid that encodes a calbindin molecule, and
 b) a semipermeable composition that encloses the engineered beta-cell.

14. A composition according to claim 13, wherein the semipermeable composition that encloses the engineered beta-cell is a porous matrix made of a non-toxic biocompatible polymer, wherein the pore structure and size of the matrix permits the diffusion of glucose and nutrients into the matrix, and the diffusion of insulin and waste products out of the matrix.

15 The composition of claim 13 wherein the matrix is produced by:
 (a) polymerizing polymer precursors in an aqueous solution containing matrix polymer precursors and viable engineered beta-cells, to form a shape-retaining solid matrix comprising viable cells and matrix polymer; and,
 (b) removing unpolymerized gel precursors from the matrix, and wherein the conditions and reagents are selected to not significantly impair the viability of the beta-cells.

16. The composition of claim 13, wherein the matrix polymer precursor is selected from the group consisting of plasma, fibrinogen, casein, fibrin, limulus lysate, milk protein, collagen, agarose, carrageenan, agar, alginate, guar gum, gum arabic, pectin, tragacanth gum, xanthan gum, and mixtures thereof.

17. A composition according to claim 13, wherein said engineered beta-cell is selected from the group consisting of an engineered primary isolate, or an insulinoma.

UNITED STATES PATENT AND TRADEMARK OFFICE
CERTIFICATE OF CORRECTION

PATENT NO. : 6,319,495 B1
DATED : November 20, 2001
INVENTOR(S) : Pollock et al.

It is certified that error appears in the above-identified patent and that said Letters Patent is hereby corrected as shown below:

18. A composition of claim 13 wherein said composition is stably maintained in a mammal.

19. A composition according to claim 18 wherein said mammal is a human patient. --

Signed and Sealed this

Second Day of July, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 2280 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
TGTAAATACA GGGCTGAAAG TGGGAGTGGC GCTCCCTCTT CCTGTTATCC CCTTGGCTCA      60

GCCTCACTGC CTGATAGAAA TGTTTCTAAT ATGGCACCTG GTCACAGTCC ATTGTAGCTG     120

AACTCCCAGG TCCTGCACTG TACAACCCTC ACCTTCCCAG TTCCCTTACC ACCTAATAAA     180

GGGCCTGCCT CCGGACAGCG CCCGGCCCGC CGCGCCCAGC TCAGCCTGCT CAGCCCTCTG     240

GTCCCGAGGT TCCGCTCAGC GCTCTCTCAA ACTAGCCGCT GCACCATGGC AGAATCCCAC     300

CTGCAGTCAT CTCTGATCAC AGCCTCACAG TTTTTTGAGA TCTGGCTTCA TTTCGACGCT     360

GATGGAAGTG GTTACCTGGA AGGAAAGGAG CTGCAGAACT TGATCCAGGA GCTTCTGCAG     420

GCACGAAAGA AGGCTGGATT GGAGCTATCA CCTGAGATGA AAACCTTTGT GGATCAATAT     480

GGGCAGAGAG ATGATGGGAA AATAGGAATT GTAGAGTTGG CCCATGTCTT ACCCACCGAA     540

GAGAATTTCC TGCTGCTCTT TCGATGCCAG CAACTGAAGT CCTGCGAGGA ATTCATGAAG     600

ACTTGGAGAA AGTATGACAC TGACCACAGT GGCTTCATAG AAACGGAGGA ACTTAAGAAC     660

TTTCTTAAGG ACCTGCTAGA GAAAGCAAAC AAGACCGTGG ATGATACGAA ACTTGCTGAG     720

TACACAGACC TCATGCTGAA GCTGTTCGAC TCAAATAATG ATGGGAAGCT GGAGCTGACA     780

GAGATGGCCA GGTTACTACC AGTGCAGGAA AATTTCCTTC TTAAATTCCA GGGAATCAAA     840

ATGTGTGGGA AAGAGTTCAA TAAGGCTTTT GAGTTATATG ATCAGGATGG CAACGGATAC     900

ATAGATGAAA ATGAGCTGGA TGCCTTACTG AAAGACCTGT GTGAGAAAAA CAAACAGGAA     960

TTGGATATTA ACAATATTTC TACATACAAG AAGAACATAA TGGCCTTGTC GGATGGAGGG    1020

AAGCTGTACC GAACAGATCT TGCCCTTATT CTCTCTGCTG GGGACAACTA GAGTTGGTGG    1080

CCACAACCAC TTGCTAGTGA TACATTGTAT CTAAAACCAT AACTGTGCGC TATAAAGGAG    1140

TAGGCTGTAT TTTCTTTTAT ATCTGTAAAT TCTACTGCAT ATAGAGAATT ATCCAGGATG    1200

TGTGGCACAT TCTTTTCTGC TTGTTTCTAT ACTGTTTGTA ATGTACAGTT TTTGTAAGCA    1260

TATAATTGAA AAGAAGAAAG TCTATGCTTA GGCCAGTCAG TATAATCCAT TTTCAAAGAT    1320

GAATCTAACA TGATTCTGCT TTCATAAATA CAGATGAACA CTTGGATTTC CCTAAAACTC    1380

TACCATCTCA ACAATTCTAG TGTCAGATGT GTAAATGCAC AGCTGTCAGT GAGTAAAAGA    1440

ATAATTCATG ACAAGCCAAG TGTTTTTTAA TTTAGGCAAT CATAGAACTG TCCCACAAAG    1500
```

```
CACTTCTGTG CGTTTTCCAT CTAGTGGAAG GGATGTGCTT CTGCTTGTGA AGCACCAAAT    1560

GTCAATAGTT AACTATGGCT TTATCATAAA ACGATCTCCC TAGAGATTTA ATTTACTGAT    1620

CAGTGGCATG TCTACTGCTT GAATAGATAC CACACTGTTG GTTCAAGCTG GCTTGGTGGC    1680

AAGGGAAGGT AGCCAGATGA CACATAAATC TGTCTGATAC TATGCCTATA TTTCCAAGAA    1740

GTCTATTGCA GAGAGTATGA CCTTAGCCCA TTTTCTAAAT TATTTTCATG TGTTCCAGAT    1800

GACAATTATT CTAGTAAACT GCTGTTTTGT GTCATATTCT GTGTGTACTC TCTGATTAAA    1860

TTCAATGTAC CTCTGAGGCC TGTCGCAGTT GGGCTCCGGC TCCTTTGCGG AGCACCATGT    1920

CGCAGAGGGG GAGGAGACCC TGCAGGGCGC CTGGGTAGAA CTGCACTTCA GCAATGGGAA    1980

TGGGAGCAGC GTTCCAGCTT CCGTCTCTAT TTATAATGGT GACATGGAAA AATACTGCT    2040

GGATGCGCAG ATGAATCTGG ACGAAGCATC TCCAAGAGCT CTCACTGTGA CAGCCCACCT    2100

CGCTCCCAGA CACCACAAGA TACCAACAAG AGCTGAAATA GCACCACACG TTTGGTGAGA    2160

AAAAACAGCA TGTGTGTCTG AGGAAGATTA TATTGAGAGA AGAAGAGAAG TTGAAAGTAT    2220

CCTGAAGAAA ACTCAGATTG GATATGGGAT TGGTCAAGTC GGCCAGAAAA TGTTCCCCCC    2280

(2) INFORMATION FOR SEQ ID NO: 2:

(i) SEQUENCE CHARACTERISTICS:
        (A) LENGTH: 2376 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

CCAGACACAC ACCCCGCTGT ACAATGGCAG AATCCCACCT GCAGTCATCC CTCATCACAG      60

CCTCACAGTT TTTCGAGATC TGGCTCCATT TCGACGCTGA CGGAAGTGGT TACCTGGAAG    120

GAAAGGAGCT GCAGAACTTG ATCCAGGAGC TCCAGCAGGC GCGAAAGAAG GCTGGATTGG    180

AGTTATCACC TGAAATGAAA ACTTTTGTGG ATCAGTATGG GCAAAGAGAT GATGGAAAAA    240

TAGGAATTGT AGAGTTGGCT CACGTATTAC CCACAGAAGA GAATTTCCTG CTGCTCTTCC    300

GATGCCAGCA GCTGAAGTCC TGTGAGGAAT TCATGAAGAC ATGGAGAAAA TATGATACTG    360

ACCACAGTGG CTTCATAGAA ACTGAGGAGC TTAAGAACTT TCTAAAGGAC CTGCTAGAAA    420

AAGCAAACAA GACTGTTGAT GACACAAAAT TAGCCGAGTA TACAGACCTA ATGCTGAAAC    480

TATTTGATTC AAATAATGAT GGGAAGCTGG AATTAACTGA GATGGCCAGG TTACTACCAG    540

TGCAGGAGAA TTTTCTTCTT AAATTCCAGG GAATCAAAAT GTGTGGGAAA GAGTTCAATA    600

AGGCTTTTGA GCTGTATGAT CAGGACGGCA ATGGATACAT AGATGAAAAT GAACTGGATG    660

CTTTACTGAA GGATCTGTGC GAGAAGAATA AACAGGATCT GGATATTAAT AATATTACAA    720

CATACAAGAA GAACATAATG GCTTTGTCGG ATGGAGGGAA GCTGTACCGA ACGGATCTTG    780

CTCTTATTCT CTGTGCTGGG GATAACTAGA GTTGGTGGCC GCAACCACTT GCTAGTGATA    840

CACTGTATCT AAAAAATAAC TGTGCACTAT AAGGGAGTAG GCTGTATTTT CTTTTATATC    900

TGTAAATTTA ACTGCATATA GATAATTATC CAGGATGTGT GGCTCATTCT TTTCAGCTTG    960

TTTCTATACT GTTTGTAATA TACAGTTTTT GTAACCATAT GATTGAAAAG AAGAAAGTCT   1020

ATGCTTAGGC CAGTCAGTAC ACCCAATTTT AAAAAATAAC ATATTCTTGC TTTCACAAAT   1080

ATAGTTGAAC AAGATTTCCC TAAAAATTCC ACCAGGATTA ATCTCTAAAA TTCTAGTCTC   1140

TGATTTGCAA ATGCACATTT GTCACTGAAT AATGGAATTA TGTATAACAA GCCAAACATT   1200
```

```
CTTATTTTAG ACAACCATAG AACTGTCCCA CAAAATATTT CTAAGCTTAT TTCTAACTAT    1260

TAGGAGGAAT GTGCTTTTCC ATCTAAAATA CTCACCAAAA TATAGTTAAT TGTGGCTTTA    1320

TGAAGTTAAC AGTCTCATTA CAGATTTAGT TTACCAATCA ACAGCATGTC TACTGCTTGG    1380

ATCCATACAA AACTATCGGT TCAAGTTGAT GTGACAAGGG AAGGGAGCAC CAGATGACAC    1440

ATAAATCTGT CTGATTCTAT GCCTGTATTT CCAACAAACT TACTGTCAGA GAATATGACC    1500

TAAATCCATT TTCTAAACTG TTTTCATGTG TTGCAAATTA TTCTAGTCAA CTGCTGTTTT    1560

ATGTCATACT CTGTGTAATC TCTGATTAAA TTTAATATAC TGCATATCCT GGTGTCTAGT    1620

TTGCATACTT CCTGGATTTT CTTTCTATGT AGAACTGTTC ATTTCCACCA AGGGTATCTG    1680

CTGCCTCTGA AAATATTTTT TTCTAGCTAT AACAACTCTA TTTTTTACTA CATAATTAAA    1740

TTTTAATGTA AAATTCATAG CATCCTGATT ATTGAATGTT ATATCATCAA TACTTTTGTG    1800

TATTCTGTGG ATTCTATATT TCATATTGAG ATCAGCATTC AAAATAGTTC TATTTCTATC    1860

TGCAAATAGT TTCAAATGAG TTTAAAAAAA TAACATCTGA AAAGAAATGC TAATGTAATC    1920

ATTTATCTTA TCTAGCAAGA AGATTCTAAA ACATTCTTTA ACATACATCT AAGTCAGTTT    1980

CACATATTTG TAGCTAGAAT ATCCTATACT GGTTATAGTT GATATGTAAC AGTTGGTGAT    2040

TTTAGATTTC TTTGATTGTG AAACAGGGAG CTATGAGAGA TGTGTCCATG TGAAATTTAC    2100

AGTTACTGCC TAGGAGTTAA TGATCGTTCT GGGTCAGCTT GAATGTCCCC ATTCTATAAA    2160

TTCAACACTT ATTTTCTGAA TTCATAAAAA TAACCAAAAA ATGTGAGCTA TAATGTTTCC    2220

CTCAAGAACA AACAGAAACG AGATTTGCCA AAAACTAAAA TTCAACAAAT GATGTTGAGT    2280

GGGAGATTGG CTTTGCCTTT AGCGTGTAAA TGGAAGCACT GCCATTAGAC TGAATTTAAC    2340

TACTAAGAAT AAATAAAGAA GAAAATAACC TTAAAA                              2376

(2) INFORMATION FOR SEQ ID NO: 3:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CATCATCAAT AATATACCTT ATTTTGGATT GAAGCCAATA TGATAATGAG GGGGTGGAGT      60

TTGTGACGTG GCGCGGGGCG TGGGAACGGG GCGGGTGACG TAGTAGTGTG GCGGAAGTGT     120

GATGTTGCAA GTGTGGCGGA ACACATGTAA GCGACGGATG TGGCAAAAGT GACGTTTTTG     180

GTGTGCGCCG GTGTACACAG GAAGTGACAA TTTTCGCGCG GTTTTAGGCG GATGTTGTAG     240

TAAATTTGGG CGTAACCGAG TAAGATTTGG CCATTTTCGC GGGAAAACTG AATAAGAGGA     300

AGTGAAATCT GAATAATTTT GTGTTACTCA TAGCGCGTAA TATTTGTCTA GGGCCGCGGG     360

GACTTTGACC GTTACGTGG AGACTCGCCC AGGTGTTTTT CTCAGGTGTT TTCCGCGTTC     420

CGGGTCAAAG TTGGCGTTTT ATTATTATAG TCA                                 453

(2) INFORMATION FOR SEQ ID NO: 4:

(i) SEQUENCE CHARACTERISTICS:
        (A) LENGTH: 874 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 4:

| | | | | | |
|---|---|---|---|---|---|
| GGCACATGGC | CAATGCATAT | CGATCTATAC | ATTGAATCAA | TATTGGCCAT | TAGCCATATT | 60 |
| AGTCATTGGT | TATATAGCAT | AAATCAATAT | TGACTATTGG | CCATTGCATA | CGTTGTATCC | 120 |
| ATATCATAAT | ATGTACATTT | ATATTGGCTC | ATGTCCAATA | TGACCGCCAT | GTTGACATTG | 180 |
| ATTATTGACT | AGTTATTAAT | AGTAATCAAT | TACAGGGTCA | TTAGTTCATA | GCCCATATAT | 240 |
| GGAGTTCCGC | GTTACATAAC | TTACGGTAAA | TGGCCCGCCT | GGCTGACCGC | CCAACGACCC | 300 |
| CCGCCCATTG | ACGTCAATAA | CGACGTATGT | TCCCATAGTA | ACGCTAATAG | GGACTTTCCA | 360 |
| TTGACGTCAA | TGGGAGGAGT | ATTTACGGTA | AACTGCCCAC | TTGGCAGTAC | ATCAAGTGTA | 420 |
| TCATATGCCA | AGTACGCCCC | CCATTGACGT | CAATGACGG | AAATGGCCCG | CCTGGCATTA | 480 |
| TGCCCAGTAC | ATGACCTTAC | GGGACTTTCC | TACTTGGCAG | TACATCTACG | TATTAGTCAT | 540 |
| CACTATTACC | ATGGTGATGC | GGTTTTGGCA | GTACATCAAT | GGGTGTGGAT | AGCGGTTTGA | 600 |
| CTCACGGGGA | TTTCCAAGTC | TCCACCCCAT | TGACGTCAAT | GGGAGTTTGT | TTTGGCACCA | 660 |
| AAATCAACGG | GACTTTCCAA | AATGTCGTAA | TAACTCCGCC | CCATTGACGC | AAATGGGCGG | 720 |
| TAGGCGTGTA | CAGTGGGAGG | TCTATATAAG | CAGAGCTCGT | TTAGTGAACC | GTCAGATCGC | 780 |
| CTGGAGACGC | CATCCACGCT | GTTTTGACCT | CCATAGAAGA | CACCGGGACC | GATCCAGCCT | 840 |
| CCGCGGCCGG | GAACGGTGCA | TTGGAACGCG | GATT | | | 874 |

(2) INFORMATION FOR SEQ ID NO: 5:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

| | | | | | |
|---|---|---|---|---|---|
| CCACCATGGC | AGAATCCCAC | CTGCAGTCAT | CTCTGATCAC | AGCCTCACAG | TTTTTTGAGA | 60 |
| TCTGGCTTCA | TTTCGACGCT | GATGGAAGTG | GTTACCTGGA | AGGAAAGGAG | CTGCAGAACT | 120 |
| TGATCCAGGA | GCTTCTGCAG | GCACGAAAGA | AGGCTGGATT | GGAGCTATCA | CCTGAGATGA | 180 |
| AAACCTTTGT | GGATCAATAT | GGGCAGAGAG | ATGATGGGAA | AATAGGAATT | GTAGAGTTGG | 240 |
| CCCATGTCTT | ACCCACCGAA | GAGAATTTCC | TGCTGCTCTT | TCGATGCCAG | CAACTGAAGT | 300 |
| CCTGCGAGGA | ATTCATGAAG | ACTTGGAGAA | AGTATGACAC | TGACCACAGT | GGCTTCATAG | 360 |
| AAACGGAGGA | ACTTAAGAAC | TTTCTTAAGG | ACCTGCTAGA | GAAAGCAAAC | AAGACCGTGG | 420 |
| ATGATACGAA | ACTTGCTGAG | TACACAGACC | TCATGCTGAA | GCTGTTCGAC | TCAAATAATG | 480 |
| ATGGGAAGCT | GGAGCTGACA | GAGATGGCCA | GGTTACTACC | AGTGCAGGAA | AATTTCCTTC | 540 |
| TTAAATTCCA | GGGAATCAAA | ATGTGTGGGA | AGAGTTCAA | TAAGGCTTTT | GAGTTATATG | 600 |
| ATCAGGATGG | CAACGGATAC | ATAGATGAAA | ATGAGCTGGA | TGCCTTACTG | AAAGACCTGT | 660 |
| GTGAGAAAAA | CAAACAGGAA | TTGGATATTA | CAATATTTC | TACATACAAG | AAGAACATAA | 720 |
| TGGCCTTGTC | GGATGGAGGG | AAGCTGTACC | GAACAGATCT | TGCCCTTATT | CTCTCTGCTG | 780 |
| GGGACAACTA | G | | | | | 791 |

(2) INFORMATION FOR SEQ ID NO: 6:

(i) SEQUENCE CHARACTERISTICS:
        (A) LENGTH: 139 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TGGGGATCCA GACATGATAA GATACATTGA TGAGTTTGGA CAAACCACAA CTAGAATGCA        60

GTGAAAAAAA TGCTTTATTT GTGAAATTTG TGATGCTATT GCTTTATTTG TAACCATTAT       120

AAGCTGCAAT AAACAAGTT                                                    139

(2) INFORMATION FOR SEQ ID NO: 7:

(i) SEQUENCE CHARACTERISTICS:
        (A) LENGTH: 2898 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GGAAGGTGCT GAGGTACGAT GAGACCCGCA CCAGGTGCAG ACCCTGCGAG TGTGGCGGTA        60

AACATATTAG GAACCAGCCT GTGATGCTGG ATGTGACCGA GGAGCTGAGG CCCGATCACT       120

TGGTGCTGGC CTGCACCCGC GCTGAGTTTG GCTCTAGCGA TGAAGATACA GATTGAGGTA       180

CTGAAATGTG TGGGCGTGGC TTAAGGGTGG AAAGAATAT ATAAGGTGGG GGTCTTATGT        240

AGTTTTGTAT CTGTTTTGCA GCAGCCGCCG CCGCCATGAG CACCAACTCG TTTGATGGAA       300

GCATTGTGAG CTCATATTTG ACAACGCGCA TGCCCCCATG GGCCGGGGTG CGTCAGAATG       360

TGATGGGCTC CAGCATTGAT GGTCGCCCCG TCCTGCCCGC AAACTCTACT ACCTTGACCT       420

ACGAGACCGT GTCTGGAACG CCGTTGGAGA CTGCAGCCTC CGCCGCCGCT TCAGCCGCTG       480

CAGCCACCGC CCGCGGGATT GTGACTGACT TTGCTTTCCT GAGCCCGCTT GCAAGCAGTG       540

CAGCTTCCCG TTCATCCGCC CGCGATGACA AGTTGACGGC TCTTTTGGCA CAATTGGATT       600

CTTTGACCCG GGAACTTAAT GTCGTTTCTC AGCAGCTGTT GGATCTGCGC CAGCAGGTTT       660

CTGCCCTGAA GGCTTCCTCC CCTCCCAATG CGGTTTAAAA CATAAATAAA AAACCAGACT       720

CTGTTTGGAT TTGGATCAAG CAAGTGTCTT GCTGTCTTTA TTTAGGGGTT TTGCGCGCGC       780

GGTAGGCCCG GGACCAGCGG TCTCGGTCGT TGAGGGTCCT GTGTATTTTT TCCAGGACGT       840

GGTAAAGGTG ACTCTGGATG TTCAGATACA TGGGCATAAG CCCGTCTCTG GGGTGGAGGT       900

AGCACCACTG CAGAGCTTCA TGCTGCGGGG TGGTGTTGTA GATGATCCAG TCGTAGCAGG       960

AGCGCTGGGC GTGGTGCCTA AAAATGTCTT TCAGTAGCAA GCTGATTGCC AGGGGCAGGC      1020

CCTTGGTGTA AGTGTTTACA AAGCGGTTAA GCTGGGATGG GTGCATACGT GGGGATATGA      1080

GATGCATCTT GGACTGTATT TTTAGGTTGG CTATGTTCCC AGCCATATCC CTCCGGGGAT      1140

TCATGTTGTG CAGAACCACC AGCACAGTGT ATCCGGTGCA CTTGGGAAAT TGTCATGTA       1200

GCTTAGAAGG AAATGCGTGG AAGAACTTGG AGACGCCCTT GTGACCTCCA AGATTTTCCA      1260

TGCATTCGTC CATAATGATG GCAATGGGCC CACGGGCGGC GGCCTGGGCG AAGATATTTC      1320

TGGGATCACT AACGTCATAG TTGTGTTCCA GGATGAGATC GTCATAGGCC ATTTTTACAA      1380

AGCGCGGGCG GAGGGTGCCA GACTGCGGTA TAATGGTTCC ATCCGGCCCA GGGGCGTAGT      1440

TACCCTCACA GATTTGCATT TCCCACGCTT TGAGTTCAGA TGGGGGGATC ATGTCTACCT      1500

GCGGGGCGAT GAAGAAAACG GTTTCCGGGG TAGGGGAGAT CAGCTGGGAA GAAAGCAGGT      1560

-continued

```
TCCTGAGCAG CTGCGACTTA CCGCAGCCGG TGGGCCCGTA AATCACACCT ATTACCGGGT      1620

GCAACTGGTA GTTAAGAGAG CTGCAGCTGC CGTCATCCCT GAGCAGGGGG GCCACTTCGT      1680

TAAGCATGTC CCTGACTCGC ATGTTTTCCC TGACCAAATC CGCCAGAAGG CGCTCGCCGC      1740

CCAGCGATAG CAGTTCTTGC AAGGAAGCAA AGTTTTTCAA CGGTTTGAGA CCGTCCGCCG      1800

TAGGCATGCT TTTGAGCGTT TGACCAAGCA GTTCCAGGCG GTCCCACAGC TCGGTCACCT      1860

GCTCTACGGC ATCTCGATCC AGCATATCTC CTCGTTTCGC GGGTTGGGGC GGCTTTCGCT      1920

GTACGGCAGT AGTCGGTGCT CGTCCAGACG GGCCAGGGTC ATGTCTTTCC ACGGGCGCAG      1980

GGTCCTCGTC AGCGTAGTCT GGGTCACGGT GAAGGGGTGC GCTCCGGGCT GCGCGCTGGC      2040

CAGGGTGCGC TTGAGGCTGG TCCTGCTGGT GCTGAAGCGC TGCCGGTCTT CGCCCTGCGC      2100

GTCGGCCAGG TAGCATTTGA CCATGGTGTC ATAGTCCAGC CCCTCCGCGG CGTGGCCCTT      2160

GGCGCGCAGC TTGCCCTTGG AGGAGGCGCC GCACGAGGGG CAGTGCAGAC TTTTGAGGGC      2220

GTAGAGCTTG GGCGCGAGAA ATACCGATTC CGGGGAGTAG GCATCCGCGC CGCAGGCCCC      2280

GCAGACGGTC TCGCATTCCA CGAGCCAGGT GAGCTCTGGC CGTTCGGGGT CAAAAACCAG      2340

GTTTCCCCCA TGCTTTTTGA TGCGTTTCTT ACCTCTGGTT TCCATGAGCC GGTGTCCACG      2400

CTCGGTGACG AAAAGGCTGT CCGTGTCCCC GTATACAGAC TTGAGAGGCC TGTCCTCGAG      2460

CGGTGTTCCG CGGTCCTCCT CGTATAGAAA CTCGGACCAC TCTGAGACAA AGGCTCGCGT      2520

CCAGGCCAGC ACGAAGGAGG CTAAGTGGGA GGGGTAGCGG TCGTTGTCCA CTAGGGGGTC      2580

CACTCGCTCC AGGGTGTGAA GACACATGTC GCCCTCTTCG GCATCAAGGA AGGTGATTGG      2640

TTTGTAGGTG TAGGCCACGT GACCGGGTGT TCCTGAAGGG GGGCTATAAA AGGGGGTGGG      2700

GGCGCGTTCG TCCTCACTCT CTTCCGCATC GCTGTCTGCG AGGGCCAGCT GTTGGGGTGA      2760

GTACTCCCTC TGAAAAGCGG GCATGACTTC TGCGCTAAGA TTGTCAGTTT CCAAAAACGA      2820

GGAGGATTTG ATATTCACCT GGCCCGCGGT GATGCCTTTG AGGGTGGCCG CATCCATCTG      2880

GTCAGAAAAG ACAATCTT                                                   2898
```

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
GATCACCATG GCTTCGTACC CCTGCC                                            26
```

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
ACGTAGGATC CCAACACGAT GTTTGTGC                                          28
```

(2) INFORMATION FOR SEQ ID NO: 10:

```
        (i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 10:

CTAGCTCGAG CAATTCCGCC CCTCTCC                                               27

(2) INFORMATION FOR SEQ ID NO: 11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 11:

GCATCCATGG TATTATCGTG TTTTTC                                                26

(2) INFORMATION FOR SEQ ID NO: 12:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 12:

AGCTAAGCTT CCACCATGGC AGAATCCCAC CTG                                        33

(2) INFORMATION FOR SEQ ID NO: 13:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 13:

ACTCGCGGCC GCCTAGTTGT CCCCAGCAGA G                                          31
```